(12) United States Patent
Kantorovich

(10) Patent No.: US 6,221,019 B1
(45) Date of Patent: Apr. 24, 2001

(54) ULTRASONIC DEVICE FOR DETERMINING BONE CHARACTERISTICS

(75) Inventor: Edward Kantorovich, Rehovot (IL)

(73) Assignee: Sunlight Ultrasound Technologies Limited, Rehovot (IL)

( * ) Notice: Subject to any disclaimer, the term of this patent is extended or adjusted under 35 U.S.C. 154(b) by 0 days.

(21) Appl. No.: 09/051,176

(22) PCT Filed: Oct. 3, 1996

(86) PCT No.: PCT/IL96/00121

§ 371 Date: Apr. 3, 1998

§ 102(e) Date: Apr. 3, 1998

(87) PCT Pub. No.: WO97/13145

PCT Pub. Date: Apr. 10, 1997

Related U.S. Application Data

(60) Provisional application No. 60/004,771, filed on Oct. 4, 1995.

(30) Foreign Application Priority Data

Jan. 8, 1996 (IL) .......................................................... 116701

(51) Int. Cl.⁷ ........................................................ A61B 8/02
(52) U.S. Cl. ............................................ 600/449; 600/438
(58) Field of Search .................................... 600/437–438, 600/440, 442, 443, 447, 449; 73/597, 599

(56) References Cited

U.S. PATENT DOCUMENTS

| | | |
|---|---|---|
| 3,127,950 | 4/1964 | Itria ............................................ 181/5 |
| 3,512,400 | 5/1970 | Lynnworth ............................. 73/67.5 |

(List continued on next page.)

FOREIGN PATENT DOCUMENTS

| | | |
|---|---|---|
| 34 41 894 | 7/1986 | (DE) . |
| 4-054944 | 2/1992 | (JP) . |
| 234609 | 1/1969 | (SU) . |
| 220428 | 11/1970 | (SU) . |
| 1159556 | 6/1985 | (SU) . |
| 1172534 | 8/1985 | (SU) . |
| 1175435 | 8/1985 | (SU) . |
| 1244502 | 7/1986 | (SU) . |
| 1308319 | 5/1987 | (SU) . |
| 1420383 | 8/1988 | (SU) . |
| WO 97/29678 | 8/1997 | (WO) . |

OTHER PUBLICATIONS

C. Hastings et al., "Inspection, Processing and Manufacturing Control of Metal by Ultrasonic Mehtos," Symposium on Ultrasonic Testing, 52nd Annual Meeting of the American Society for Testing Materials, Jun. 28, 1949. pp. 14–61.

(List continued on next page.)

Primary Examiner—Francis J. Jaworski
(74) Attorney, Agent, or Firm—Kenyon & Kenyon

(57) ABSTRACT

A method for determining, through an interposing medium, the mechanical properties of a solid having a surface, including transmitting a first ultrasonic wave along a transmission path from a first location through the interposing medium, along the surface and from the surface through the interposing medium to a second location; measuring the travel time of the first wave along the transmission path; measuring the thickness of the interposing medium; measuring the acoustic velocity of the interposing medium; and calculating the acoustic velocity in the solid based on the distance between the locations, the thickness of the interposing medium and the acoustic velocity in the interposing medium.

95 Claims, 15 Drawing Sheets

U.S. PATENT DOCUMENTS

| | | | | |
|---|---|---|---|---|
| 3,720,098 | | 3/1973 | Dixon | 73/67.7 |
| 3,847,141 | | 11/1974 | Hoop | 128/2 |
| 4,361,154 | | 11/1982 | Pratt, Jr. | 128/660 |
| 4,421,119 | | 12/1983 | Pratt, Jr. | 128/660 |
| 4,566,459 | * | 1/1986 | Umemura et al. | 600/443 |
| 4,597,292 | | 7/1986 | Fujii et al. | 73/599 |
| 4,640,132 | | 2/1987 | Flora et al. | 73/602 |
| 4,653,505 | * | 3/1987 | Iinuma | 600/449 X |
| 4,669,482 | * | 6/1987 | Ophir | 600/449 |
| 4,752,917 | | 6/1988 | Dechape | 367/125 |
| 4,774,959 | | 10/1988 | Palmer et al. | 128/660.06 |
| 4,779,623 | * | 10/1988 | Sumino et al. | 600/440 |
| 4,913,157 | * | 4/1990 | Pratt, Jr. et al. | 600/449 |
| 4,926,870 | | 5/1990 | Brandenburger | 128/660.01 |
| 4,930,511 | | 6/1990 | Rossman et al. | 129/661.03 |
| 4,941,474 | | 7/1990 | Pratt, Jr. | 128/660.06 |
| 5,143,069 | | 9/1992 | Kwon et al. | 128/660.01 |
| 5,269,309 | | 12/1993 | Fort et al. | 128/660.01 |
| 5,343,863 | * | 9/1994 | Wiener et al. | 600/449 |
| 5,396,891 | | 3/1995 | Whitney et al. | 128/660.01 |
| 5,426,979 | * | 6/1995 | Kantorovich et al. | 600/437 |
| 5,488,953 | | 2/1996 | Vilkomerson | 18/661.08 |
| 5,488,956 | * | 2/1996 | Bartelt et al. | 600/459 |

OTHER PUBLICATIONS

R.P. Heaney et al., "Osteoporotic Bone Fragility: Dectection by Ultrasound Transmission Velocity", JAMA, vol. 261, No. 20, May 26, 1989, pp. 2986–2990.

M. Greenfield et al., "Measurement of the Velocity of Ultrasound in Human Cortical Bone In Vivo", Radiology, Col. 138, Mar. 1981, pp. 701–710.

R. N. McCartney et al., "Combined 2.25 MHz Ulstrasound Velocity and Bone Mineral Density Measurements in the Equine Metacarpus and their In Vivo Applicaitons", Medical and Biological Engineering and Computation, vol. 25, Nov. 1987, pp. 620–626.

Catalogue: DBM Sonic 1200, Bone Quality Assessment at the Touch of the Phalanx, IGEA. Dec. 1995.

R. Graff, "Wave Motion in Elastic Solids", 1975.

* cited by examiner

ULTRASONIC DEVICE FOR DETERMINING BONE CHARACTERISTICS

This application claims priority of Provisional Application 60/004,771 4 Oct. 1995.

FIELD OF THE INVENTION

The present invention relates to Instrumentation for non-destructive measurement of mechanical properties of materials generally and to instrumentation for non-invasive measurement of the mechanical properties of bone and bone quality.

BACKGROUND OF THE INVENTION

It is known in the art that the velocity of a sound wave in a material depends on the mechanical properties of the material. This phenomena is described, for example, by C. H. Hastings and S. W. Carter in an article entitled "Inspection, Processing and Manufacturing Control of Metal by Ultrasonic Methods," *Symposium on Ultrasonic Testing*, 52nd Annual Meeting of the American Society for Testing Materials, Jun. 28, 1949, pp. 16–47.

U.S. Pat. Nos. 3,720,098, 3,228,232, 3,288,241, 3,372,163, 3,127,950, 3,512,400, 4,640,132, 4,597,292 and 4,752,917 describe the state of the art of non-destructive testing using ultrasound.

A sound wave which reaches a semi-infinite solid at an angle will typically propagate through and along the solid as three waves, namely, longitudinal, transverse and surface waves, wherein each wave has a different velocity. As described by Hastings and Carter, the velocities of the three waves are:

$$V_L = \sqrt{\frac{E(1-\sigma)}{\text{rho}(1+\sigma)(1-2\sigma)}} \quad (1)$$

$$V_T = \sqrt{\frac{E}{2(1+\sigma)\text{rho}}} \quad (2)$$

$$V_S = \alpha V_T \quad (3a)$$

$$\alpha = \frac{0.87 + 1.12\sigma}{1+\sigma} \quad (3b)$$

where $V_L$, $V_T$, and $V_S$ are, respectively, the velocities of the longitudinal, transverse and Raleigh surface waves, and E, $\sigma$ and rho are, respectively, the Young's Modulus, the Poisson's ratio of lateral contraction to longitudinal extension and the mass density of the material. Equation (3b) is an empirical relationship as defined on page 326 of *Wave Motion in Elastic Solids*, by Karl F. Graff, published by the Clarendon Press, Oxford England in 1975.

In ultrasonic measurement of the condition of bone, typically only the velocity of the longitudinal wave is used. In an article entitled, "Osteoporotic Bone Fragility: Detection by Ultrasound Transmission Velocity," R. P. Heaney et al., *JAMA*, Vol. 261, No. 20, May 26, 1989, pp. 2986–2990, the Young's Modulus of bone, E, is given empirically as:

$$E = K(\text{rho})^2 \quad (4a)$$

The velocity of the longitudinal sound wave in the bone is given as:

$$V_L = \sqrt{(E/\text{rho})} = \sqrt{(K \cdot \text{rho})} \quad (4b)$$

where K is a constant which incorporates a number of factors, such as spatial orientation of the bone structures, inherent properties of the bone material and fatigue damage. Thus, the velocity of a longitudinal wave is a function of the mass density and can be used as an indicator of the quality of bone.

The following articles also discuss ultrasonic measurement of bone condition both in vivo and in vitro:

"Measurement of the Velocity of Ultrasound in Human Cortical Bone In Vivo," M. A. Greenfield, et al., Radiology Vol 138, March 1981, pp. 701–710; and "Combined 2.25 MHz ultrasound velocity and bone mineral density measurements in the equine metacarpus and their in vivo applications," R N. McCartney and L. B. Jeffcott, *Medical and Biological Engineering and Computation*, Vol. 25, 1987, Nov. 1877, pp. 620–626.

In order to perform in vivo ultrasonic measurements of the mechanical properties of bone, it is necessary to transmit an ultrasonic wave through the soft tissue surrounding the bone. Unfortunately, the thickness of the soft tissue varies along the length of the bone. This thickness variation can affect the accuracy of the ultrasound propagation time measurement through the bone. In the abovementioned articles, the thickness of the soft tissue is either ignored or an attempt is made to cancel the effects of the soft tissue. In the articles describing in vitro experiments, the soft tissue is removed from the bone.

Russian patents 1,420,383, 1,308,319, 1,175,435, 1,324,479, 1,159,556 and 1,172,534 and U.S. Pat. Nos. 4,926,870, 4,361,154, 4,774,959, 4,421,119, 4,941,474, 3,847,141, 4,913,157 and 4,930,511 describe various systems for measuring the strength of bone based on the velocity $V_L$. These systems typically have one ultrasonic signal transmitter and at least one ultrasonic signal receiver.

Russian patents 1,420,383, 1,308,319 and 1,175,435 attempt to solve the problem of the unknown thickness of the soft tissue by assuming values for the thickness of the soft tissue in the area of the measurement or by assuming that the thickness variation is small over the distance between two ultrasonic signal receivers.

Russian patent 1,342,279 utilizes two receivers and a single transmitter and calculates an average group speed through the bone based on the known distance between the two receivers.

Russian patent 1,159,556 defines zones of a bone and the condition of a bone is determined by the difference between the maximum and minimum amplitude of the ultrasound signals measured, different zones having different velocities. It appears that this measurement is performed on an excised bone.

Russian patent 1,172,534 describes a system which compares the ultrasound signal of a healthy bone with that of an unhealthy bone and from the comparison, produces a diagnosis of the extent of disease in the unhealthy bone.

U.S. Pat. Nos. 4,926,870, 4,421,119 and 3,847,141 describe systems which places a receiver and a transmitter on opposite sides of a bone. U.S. Pat. No. 4,926,870 also compares the resultant signal with a canonical waveform, thereby to classify the health of the bone.

U.S. Pat. Nos. 4,913,157, 4,774,959 and 4,941,474 describe systems which transmit an ultrasonic signal with a spectrum of frequencies.

U.S. Pat. No. 4,930,511 describes a system which is placed around a standard inanimate homogeneous material of known acoustic properties before it is placed around a bone.

U.S. Pat. No. 5,143,072, the disclosure of which is incorporated herein by reference, describes a method of overcoming the effects of the unknown thickness of the intervening soft tissue. FIG. 1A, which illustrates the method of this patent, shows an ultrasonic transmitter 2 and two ultrasonic receivers 4 and 6, all of which are collinear. Transmitter 2 transmits an ultrasonic wave through soft tissue 22 towards a bone 18. The first signal received at receiver 4 passes through the fastest path. This path includes a first soft-tissue path portion 8, a bone surface portion 10 and a second soft-tissue path portion 14. An angle 23 between path 8 and path 10 is determined by the ratio between the acoustic velocity in bone 18 and the acoustic velocity in soft-tissue 22. The first signal received by receiver 6 passes through first soft-tissue path portion 8, bone surface portion 10, an additional bone path portion 12 and a third soft-tissue path portion 16. The propagation times for the first received signals at receivers 4 and 6 are measured. If receivers 4 and 6 are aligned so that path 14 and path 16 are of the same length, subtracting the two signal propagation times yields the signal propagation time in bone portion 12. Since bone portion 12 has the same length as the distance between receiver 4 and receiver 6, the acoustic velocity in bone portion 12 can be determined.

FIG. 1B shows a method disclosed by the '072 patent for assuring that path 16 and path 14 have the same length Receivers 4 and 6 are also transmitters, and they are used to measure the wave propagation times along paths 30 (and 32) between receivers 4 (and 6) and bone 18. In an additional embodiment disclosed, transmitter 2 and receivers 4 and 6 are mounted on a rocker, which compresses soft tissue 22 when it rocks, such that when the propagation times along paths 30 and 32 are found to be equal, acoustic bone velocity is determined.

However, even this method has several serious shortcomings. First, soft tissue velocity is not a constant, rather, it varies with the type of soft tissue. Since the propagation paths 30 and 32 are not the same as paths 14 and 16, the propagation times along paths 14 and 16 may be unequal and the calculated acoustic bone velocity is not correct, even if the propagation times along paths 30 and 32 are equal. Second, the above described method requires a relatively long portion of flat bone. Thus, only a small number of bones can be tested, using this method, such as the tibia In addition, since high frequency ultrasonic waves are very lossy, it is not practical to use them for this method. Third, the spatial resolution of this method is relatively low, approximately 2–5 cm.

SUMMARY OF THE INVENTION

It is an object of some aspects of the present invention to provide a method of acoustic bone velocity determination which has a high resolution In addition, a small portion of bone can be measured, so that almost all the bones of the human body can be measured using a preferred embodiment of the present invention.

In a preferred embodiment of the present invention, a transmitter and a receiver are placed on the skin of a patient facing a bone. The acoustic velocity in a bone is measured by:

(1) transmitting a first ultrasonic signal along a mission path from the transmitter to the bone through the soft tissues surrounding the bone, along the surface of the bone and back through the soft tissue to the receiver;

(2) measuring the travel time of the fastest signal between the transmitter and the receiver; and (3) calculating the acoustic velocity of the bone based on the distance between the transmitter and the receiver, the thickness of the soft tissue and the acoustic velocity in the soft tissue.

A preferred method of calculating both the acoustic velocity of the soft tissue and its thickness utilizes reflected waves. A transmitter and a transmitter/receiver are placed a known distance apart on the skin, such that the fastest path from the transmitter to the transmitter/receiver does not pass through the bone. Rather, the fastest signal is reflected from a point on the bone to the transmitter/receiver. It should be noted that the distance between the transmitter and the transmitter/receiver can be very small. The propagation times of a signal sent from the transmitter to the transmitter/receiver and of a signal sent by the transmitter/receiver and reflected back to the same transmitter/receiver by the bone, are measured.

A right triangle is formed by the following three line segments:

(a) a first side $s_1$ which is the shortest line connecting the transmitter and the bone;

(b) a second side $s_2$ which is a line starting at the transmitter/receiver and extending half the distance between the transmitter and the transmitter/receiver; and (c) a hypotenuse H which is the line between the transmitter and the signal reflection point on the bone.

Assuming that the thickness of the soft tissue under the transmitter is equal to the thickness under the transmitter/receiver, $s_1$ has the same length as the distance between the transmitter/receiver and the bone. It can also be assumed that the average soft-tissue acoustic velocity is the same along all the paths being measured, since they are very close together. Thus, the ratio between the first side and the hypotenuse is equal to the ratio between the measured propagation times. The length of the second side is easily calculated using the known formula: $s_1^2+s_2^2=H^2$. Since the lengths $s_1$, $s_2$ and H are actually expressed as times, $s_2$ is actually the time it would have taken the signal to travel half the known distance between the transmitter and the transmitter/receiver if the path were in the soft tissue. Thus, the soft tissue acoustic velocity is determined. The thickness of the soft tissue is now easily determined using the measured propagation time from the transmitter/receiver to the bone and back.

Alternatively, other methods of velocity and thickness determination are used. For example, an X-ray image is used to determine the thickness, and the velocity is determined by measuring the amount of time it takes for a signal to travel from a transmitter/receiver, to the bone, and back, along the measured path.

Preferably, the thickness is measured at the point at which the signal from the transmitter to the receiver enters the bone. Additionally or alternatively, the thickness of the soft tissue is measured at the point where the signal from the transmitter to the transmitter/receiver is reflected from the bone.

Preferably, the paths of the signal from the transmitter to the transmitter/receiver overlaps with the path of the signal from the transmitter to the receiver.

It should be appreciated that instead of imaging human or animal flesh, the preferred embodiments can be used for analyzing wood, plastic metal and composite materials that are coated with an outer coating of a different material.

It should be appreciated that the above described methods of soft tissue velocity and soft tissue thickness determination are also useful in increasing the accuracy of prior art acoustic bone velocity determination methods.

A typical resolution achievable using the above described bone acoustic velocity method is better than 1 centimeter, more typically better than 0.5 centimeters, preferably better than 3 millimeters.

Preferably, the above mentioned transmitters and receivers are mounted in a sensor having a long axis and a short axis. The sensor is preferably rocked along its long axis while a plurality of measurements are taken. Preferred bone velocity measurements are performed when the thicknesses of the soft tissues underlying the transmitter and the receiver are equal, even if the average acoustic velocity are not equal.

Additionally or alternatively, the sensor is rocked along its short axis while a plurality of measurements are taken. Preferably the dependency of the determined bone acoustic velocity on the rocking angle is determined. Typically, the maximum determined velocity is employed as the representative acoustic velocity.

There is also provided, according to a preferred embodiment of the present invention, a method of determining, through an interposing medium, the thickness of a solid, including, transmitting a broadband ultrasonic wave along a path from a first location, through the medium and along the surface of the solid, receiving the wave at a second location and analyzing the received wave to determine the difference between the travel time of the high frequency components of the wave and the travel time of the low frequency components of the wave.

There is further provided according to a preferred embodiment of the present invention a method of determining the acoustic velocity of a first soft tissue embedded in a second soft tissue, including, determining the location of the first tissue in the second tissue, determining the acoustic velocity of the second tissue along a first path and determining the acoustic velocity of the second tissue along a second path which includes the first tissue. Preferably, the first path substantially overlaps the second path.

There is also provided, according to a preferred embodiment of the present invention, apparatus for acoustic velocity determination of a solid having a surface. The apparatus comprises: a first ultrasonic unit for generating first signals and second signals through an interposing medium to the surface, wherein said second signals travel through the solid and generally parallel to said surface, a second ultrasonic unit for receiving said first signals reflected off said surface, for generating third signals through said interposing medium to said surface and for receiving said third signals reflected from said surface, a third ultrasonic unit for receiving said second signals and a control unit for measuring the shortest travel time of said first second and third signals.

There is further provided in accordance with a preferred embodiment of the present invention, apparatus for acoustic velocity determination of a solid having a surface, comprising: a first ultrasonic unit for generating a wave through an interposing medium to a surface, wherein said wave travels through said solid and generally parallel to said surface a second ultrasonic unit for receiving said wave at least one ultrasonic unit for generating waves towards said surface and receiving waves reflected from said surface and a control unit for measuring the shortest travel time of all of said waves.

Preferably, said second ultrasonic unit comprises one, two, three or four ultrasonic units.

Preferably, the receiving units do not transmit waves at times shortly before they receive waves.

There is also provided according to another preferred embodiment of the present invention apparatus comprising: a grid of piezoelectric cells for generating and receiving ultrasonic waves, a driver for said grid and a control unit for measuring the travel time of said waves, wherein some of said waves are reflected off of said surface and some of said waves travel through said solid and generally parallel to said surface.

In a preferred embodiment of the invention, a two step method is used to configure the grid. In a first step, the thickness of the underlying tissue is determined, preferably using the methods described herein. In the second step, the grid is configured so that the distances between transmitting elements and receiving elements are optimized for the tissue thickness.

In yet another preferred embodiment of the invention, the grid is operated, substantially simultaneously, in two modes. A first mode comprises ultrasonic scanning as known in the art. A second mode comprises soft tissue velocity determination and/or bone velocity determination, preferably, as described hereinabove.

Preferably, the control unit is used to calculate the acoustic velocity of the solid and/or the acoustic velocity of the interposing medium.

It should be noted that the ultrasonic units need not be collinear.

The above mentioned ultrasonic waves are preferably single frequency waves. Additionally or alternatively, the above measurements are performed simultaneously.

BRIEF DESCRIPTION OF THE DRAWINGS

The invention will be more filly understood from the following detailed description of the preferred embodiments thereof taken in conjunction with the drawings in which.

DETAILED DESCRIPTION OF THE PREFERRED EMBODIMENTS

Figure 1A:
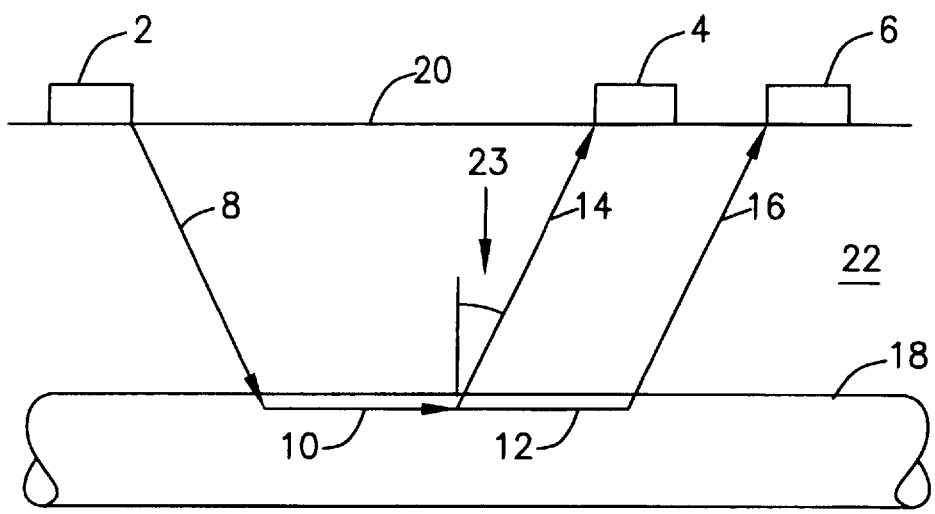
FIG. 1A shows a prior art method of acoustic bone velocity measurement.
Figure 1B:
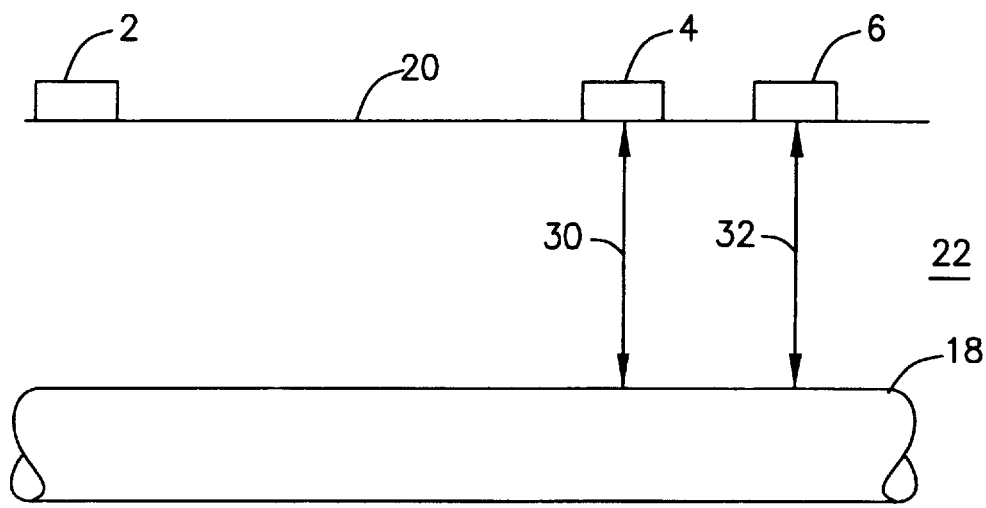
FIG. 1B shows a prior art enhancement to the method shown in FIG. 1A which includes additional measurements.
Figure 2:
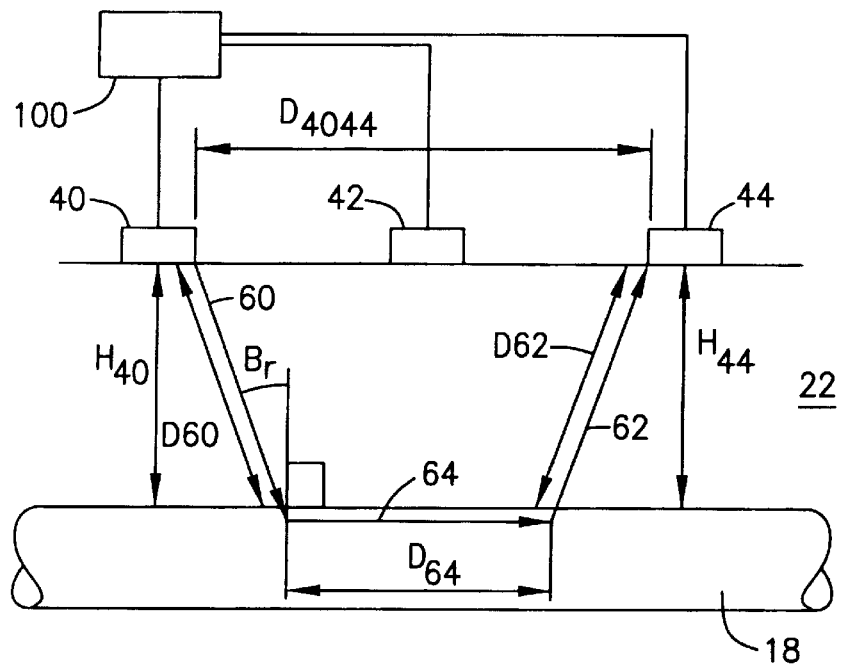
FIG. 2 shows a method of acoustic bone velocity measurement according to a preferred embodiment of the present invention.

A method of acoustic bone velocity determination according to a preferred embodiment of the present invention includes soft tissue velocity determination. FIG. 2 shows a bone 18 surrounded by soft tissue 22. To measure acoustic bone velocity, a transmitter 40 transmits a signal to a receiver 44, and a travel time $T_{total}$ is measured. Obviously, there are many paths that the signal can take from transmitter 40 to receiver 44, some of which reflect off bone 18 and some which pass along the surface of bone 18.

If a distance $D_{4044}$ between transmitter 40 and receiver 44 is long enough, the fastest path, as shown in FIG. 2, comprises three segments. A first soft tissue path segment 60, a surface bone path segment 64 and a second soft tissue path segment 62. The angle $B_r$ between segment 60 and a perpendicular to segment 64 (bone 18) is the Brewster angle, defined as:

$$B_r = \arcsin(V_{22}/V_{18})) \quad (5)$$

where $V_{22}$ is the velocity of a longitudinal wave in soft tissue 22 and $V_{18}$ is the velocity of a longitudinal surface wave in bone 18. If $D_{4044}$ is so short that a Brewster angle cannot be formed, then the fastest path is one of simple reflection off bone 18.

The acoustic velocity in bone 18 is calculated by dividing a length $D_{64}$ of bone segment 64 by the a time $T_{64}$ it took the signal to propagate across bone segment 64. However, neither $D_{64}$ nor $T_{64}$ are known. Some prior art methods estimate $V_{22}$, a distance $H_{40}$ between transmitter 40 and bone 18 and a distance $H_{44}$ between receiver 44 and bone 18. Thus, a distance $D_{60}$, which is the length of segment 60, a distance $D_{62}$ which is the length of segment 62 and their propagation times $T_{60}$ and $T_{62}$ are:

$$D_{60} = \frac{H_{40}}{\cos(B_r)} \quad (6)$$

$$D_{62} = H_{44}/\cos(B_r) \quad (7)$$

$$T_{60} = D_{60}/V_{22} \quad (8)$$

$$T_{62} = D_{62}/V_{22} \quad (9)$$

$D_{64}$ and $T_{64}$ are:

$$D_{64} = D_{4044} - (H_{40}\mathrm{tg}(B_r) + H_{44}\mathrm{tg}(B_r)) \quad (10)$$

$$T_{64} = T_{total} - (T_{60} + T_{62}) \quad (11)$$

So that $V_{18}$ is:

$$V_{18} = D_{64}/T_{64} \quad (12)$$

Solving the simultaneous equations (5)–(12) yields $V_{18}$.

Figure 3:
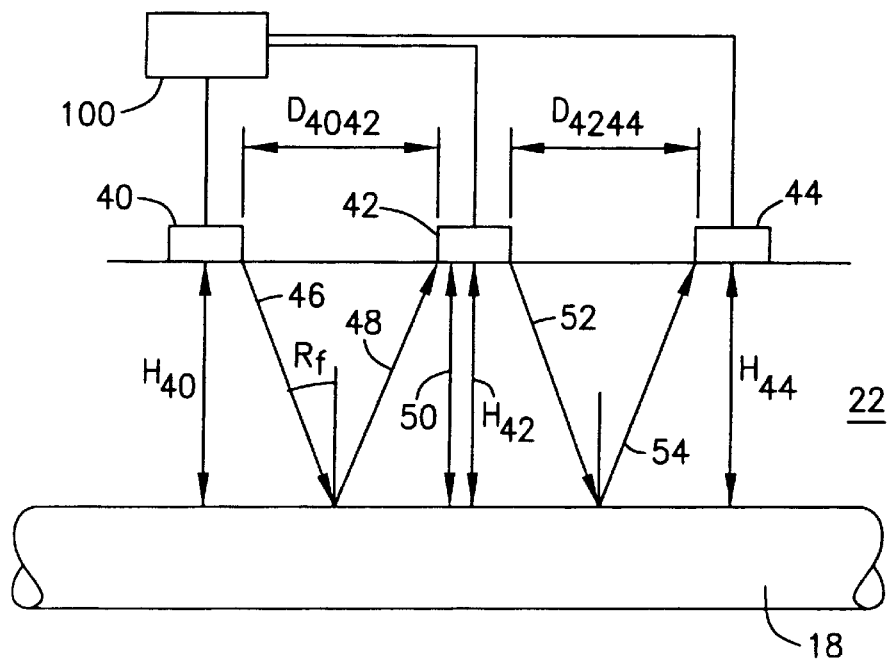
FIG. 3 shows a method of soft tissue acoustic velocity determination according to a second preferred embodiment of the present invention.

However, estimation of $H_{40}$, $H_{44}$ and $V_{22}$ is not very precise, especially since V22 changes as a function of distance from bone 18. Typically, the tissues near bone 18 are muscle and have an average velocity 10% higher than fat, which is typically deposited closer to the FIG. 3 shows a method of determining $H_{40}$, $H_{44}$ and $V_{22}$ in accordance with a preferred embodiment of the invention. A transmitter/receiver 42 is colinearly placed between transmitter 40 and receiver 44 such that the fastest path between transmitter 40 and transmitter/receiver 42 has no path segment in bone 18. The fastest path between transmitter 40 and transmitter/receiver 42, as shown in FIG. 3, comprises a first soft tissue segment 46 and a second soft tissue segment 48. A method of placing transmitter/receiver 42 in such a location is to:

(a) estimate the Brewster angle; and (b) place transmitter/receiver 42 at a location wherein a reflection angle $R_f$ which is the angle between segment 46 and a perpendicular to bone 18, is smaller than the Brewster angle.

As is known in the art, where the incidence angle is smaller than or equal to the Brewster angle, the fastest path does not pass through bone 18, but is merely reflected from it.

First, $V_{22}$ is measured. A signal is transmitted from transmitter 40 to transmitter/receiver 42 and its propagation time $T_{46}+T_{48}$ is measured. A second signal is transmitted from transmitter/receiver 42 to bone 18 and reflected back along a path segment 50. An isosceles triangle is formed by (a) the line connecting transmitter 40 and transmitter/receiver 42, which has a length $D_{4042}$;

(b) segment 46, which has a length $D_{46}$; and (c) segment 48, which has a length $D_{48}$.

Assuming that the thickness of tissue 22 is constant in the small region between transmitter 40 and titter/receiver 42, segment 50 has a length $D_{50}$ which is equal to the height of the isosceles triangle.

If we assume that the average $V_{22}$ is equal along segment 46, segment 48 and segment 50 then $D_{46}$, $D_{48}$ and $D_{50}$ are:

$$D_{46} = V_{22}*T_{46} \quad (13)$$

$$D_{48} = V_{22}*T_{48} \quad (14)$$

$$D_{50} = V_{22}*T_{50}/2 \quad (15)$$

Applying a known relationship between the sides and height of an isosceles triangle:

$$D_{4042} \div 2 = \sqrt{D_{48}^2 - D_{50}^2} \quad (16)$$

Solving equation 16 using equations 14 and 15 and using the equality between $T_{48}$ and $T_{46}$:

$$D_{4042} = 2V_{22} * \sqrt{(T_{48} + T_{46})^2 - (T_{50})^2} / 2 \qquad (17)$$

However, $T_{50}$, $T_{48}$ and $D_{4042}$ are known thus:

$$V_{22} = D_{4042} \div \sqrt{(T_{48} + T_{46})^2 - T_{50}^2} \qquad (18)$$

It should be noted that the above calculated $V_{22}$ is an average along the actual path of the signal, i.e., including the weighted values of both the velocity in fat and the velocity in muscle tissue.

$H_{44}$ is assumed to be equal to $H_{40}$ (which is equal to $D_{50}$) Thus:

$$H_{44} = H_{40} = V_{22} * T_{50} \qquad (19)$$

If a higher precision is required, or to reduce noise, $V_{22}$ is calculated a second time using the signal propagation time between transmitter/receiver 42 and receiver 44 instead of the signal propagation time between transmitter 40 and transmitter/receiver 42. Of course, the distance between transmitter/receiver 42 and receiver 44 is also such that the reflectance angle is smaller or equal to the Brewster angle. $V_{22}$ is calculated by using the average of the first and second calculations.

Alternatively to the above described method of measuring $V_{22}$, $H_{40}$ and $H_{44}$, other methods can be used. For example, $H_{40}$ and $H_{44}$ can be measured on an X-ray image or another medical image. $V_{22}$ is then measured based on the signal propagation time of the reflection from bone 18.

Figure 4A:
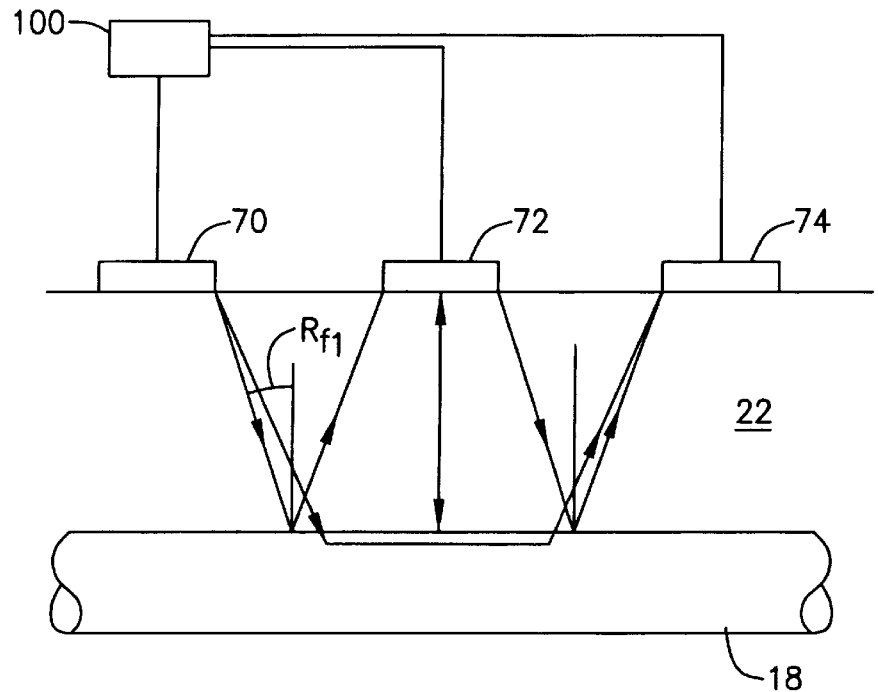
FIG. 4A shows a preferred method of acoustic bone velocity measurement combining aspects of the methods of FIGS. 2 and 3.
Figure 4B:
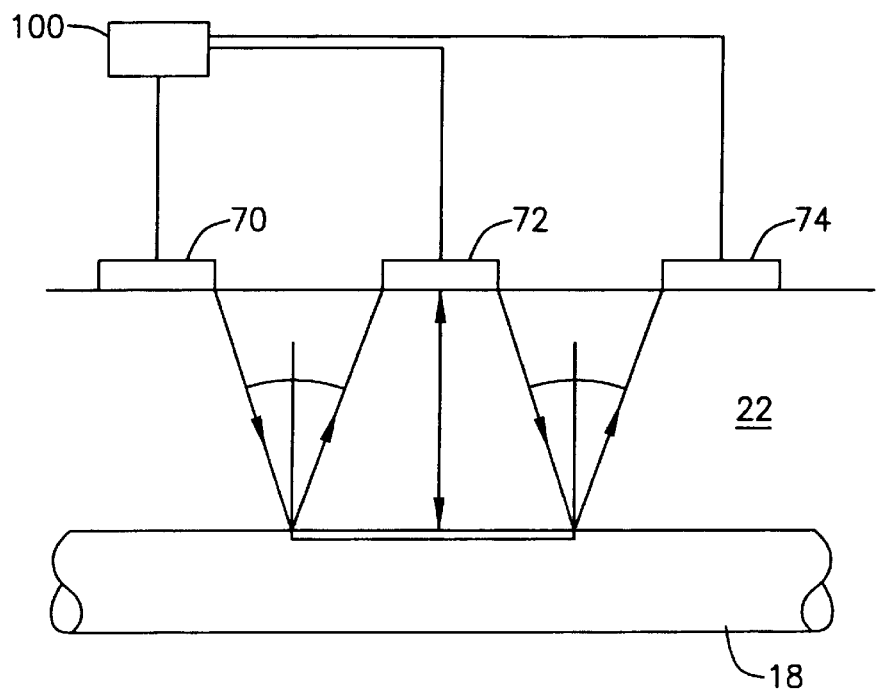
FIG. 4B shows another preferred embodiment of the invention combining aspects of the methods of FIGS. 2 and 3.

FIGS. 4A and 4B show a acoustic bone velocity measurement sensor according to another preferred embodiment of the present invention. A transmitter 70, a transmitter/receiver 72 and a receiver 74 are placed colinearly on soft tissue 22 which surrounds bone 18. As described above, the distance between transmitter 70 and transmitter/receiver 72 is such that a signal propagating from transmitter 70 to transmitter/receiver 72 does not pass through bone 18. Preferably, also the fastest path from transmitter/receiver 72 to receiver 74 does not pass through bone 18.

$V_{22}$ and the thickness of soft tissue 22 in the region near transmitter/receiver 72 are then determined as described above. The acoustic velocity in bone 18 is then determined using the above described method of sending a signal from transmitter 70 to receiver 74. Preferably, the distance between transmitter 70 and transmitter/receiver 72 is such that a signal propagating between them is reflected at an angle $R_{f1}$ which is approximately equal to the Brewster angle as shown in FIG. 4B. Thus, $V_{22}$ is measured along the same path as that of the signal for measuring the bone velocity. Since the Brewster angle in human flesh is between 20° and 28°, an angle of 24° is a good estimate, which results in near overlap of the paths.

Preferably, transmitter/receiver 72 is midway between transmitter 70 and receiver 74. Thus, if the line connecting transmitter 70 and receiver 74 is not exactly parallel to bone 18, the fact that the thickness of the soft tissue is measured in between them will tend to give a close approximation to the average velocities.

The minimal required distance of wave propagation in the bone using this method is approximately 2 to 3 millimeters. The distance between transmitter 70 and receiver 74 depends on the soft tissue thickness. Using this method, high resolution mapping of relatively uneven bones is possible.

For example, such bones include the vertebra, the small bones in the wrist and portions of bone near joints. In addition, it is possible to measure the bone velocity in both longitudinal and transverse directions, since the length of the measured bone segment can be very short.

A preferred operating frequency is between 250 and 1500 kHz. It should be noted that since the distance that the signals travel in the bone are short, frequencies higher than those used in the prior art are practical, in spite of the higher attenuation of high frequency sound waves in bone. In general, higher frequencies give more precise results than do lower frequencies. In some preferred embodiments of the present invention, the operating frequency is preferably over 2 MHz, more preferably, over 5 MHz and in some preferred embodiments of the present invention, the preferred operating frequency is over 10 MHz. Preferably, the wave is pulsed with a duration of between 2 and 150 microseconds.

The wave form used is preferably a single frequency pulsed wave, since the only aspect of the wave analyzed is the time of first reception of a signal. Alternatively, other, more complex wave forms or pulses are used and the received signals are analyzed.

Preferably, transmitter 70 and transmitter/receiver 72 are oriented to preferentially emit their signals at an angle which is the estimated Brewster angle, as known in the art. In addition, receiver 74 and transmitter/receiver 72 are preferably adapted to have a high gain for reception at the estimated Brewster angle.

Typically, when Knitter 70 and transmitter/receiver 72 are oriented at the Brewster angle, the sensor face is concave, rather than flat. Preferably, this concave space is filled with a uniform material having a known acoustic velocity. In a preferred embodiment of the invention, the acoustic velocity of the filler material is close to that of soft tissue, thus, the effect of the filler material on the calculations described herein can be ignored. Alternatively, the effect of the layer of filler material on the acoustic velocity calculations can be estimated and taken into account, either during calibration or, as described below, as the effect of the top layer in a multilayer structure.

It should be appreciated that the two steps of the above described process can be performed in either order and can also be performed simultaneously. Preferably, different frequencies are used for each signal. It should be appreciated that the ultrasound transmitter and receiver used typically has a very wide bandwidth. Thus, a plurality of wavelengths are emitted and each receiver processes its incoming signals to filter out and detect specific frequencies. Alternatively or additionally, the pulses are timed, so that no two pulses arrive together at a single receiver.

Preferably, the transmitter 70, transmitter/receiver 72 and recover 74 are controlled by a control unit 100. Thus, initiation of the above described signals, measurement of times, signal processing and velocity calculations are performed by control unit 100.

A three element sensor, such as described in reference to FIG. 4A and 4B, is preferably constructed to be less than 100 millimeters long, more preferably less than 50 millimeters long and in some preferred embodiments less than 3 millimeters long. In a specific preferred embodiment, the sensor is 32 millimeters long The maximum distance allowed between such a sensor and a bone is approximately 2 centimeters. Due to the very high accuracy requirements from such a sensor, it is preferably constructed from a material which does not substantially expand or shrink in the temperature range of 15–40° C. Such materials typically comprise a mixture of a material which expands when heated from 15 to 40° C. and a material which shrinks when heated from 15 to 40° C.

It should be appreciated, that the distance between the ultrasonic elements can be optimized for a certain expected soft tissue depth Thus, a typical operational system comprises several sensors, each suitable for a different range of depths. Alternatively, a single grid-type sensor, as described hereinbelow, is used.

Typically, the sensor is not constructed to have an exact distance between each ultrasonic element. Instead, a sensor is constructed with a precision of approximately 0.1 millimeter, and the exact distances between the elements are measured using a phantom. The results of the measurement, having a typical precision of over $2\mu$, are stored in controller 100 for use in the velocity determination as described in greater detail below. Such a phantom preferably comprises a plastic cylinder which has a cylindrical metal core with steps formed along its anus embedded within the plastic. Each step corresponds to a different known depth of the plastic overlying the metal core.

Bone acoustic velocity is typically not equal in different portions of the bone. Thus, to properly compare two bone acoustic velocity results from two different measuring sessions, the two measurements must be performed on the same portion of the bone. In particular, the location accuracy along the longitudinal axis of the bone should be on the order of 5 millimeters in long bones, such as the tibia This accuracy is easy to attain using regular positioning methods, such as marking the location with permanent marker. However, the transverse positioning accuracy must be on the order of hundreds of microns. Since achieving this accuracy is difficult, the sensor is preferably mounted on a rocker such that transmitter 70, transmitter/receiver 72 and receiver 74 are along an axis of the rocker which is parallel to bone's 18 longitudinal axis. When measuring the bone acoustic velocity, the rocker is rocked in a transverse direction and a phi of bone acoustic velocities are determined. The maximum or minimum determined value is used as the reference value for comparison to bone acoustic velocity measurements during other sessions. Additionally or alternatively, the acoustic velocity of bone 18 is measured from several sides of bone 18, since the cortex of bone 18 typically has a number of different sectors, each of which has a different hardness and acoustic velocity.

It should be appreciated that with some bones, such as the vertebra, measuring the softer sectors is more practical than measuring the harder sectors, hence the search for the minimum velocity. The minimum determined velocity is typically in the softest sector. A minimum determined velocity found at a later date is also in the softest sector, thus, the velocity measurement is repeated at the same transverse location (same sector).

Additionally or alternatively, the acquired velocity measurements are used to build a transverse velocity profile of bone 18, which is useful for bone structure analysis.

Figure 4C:
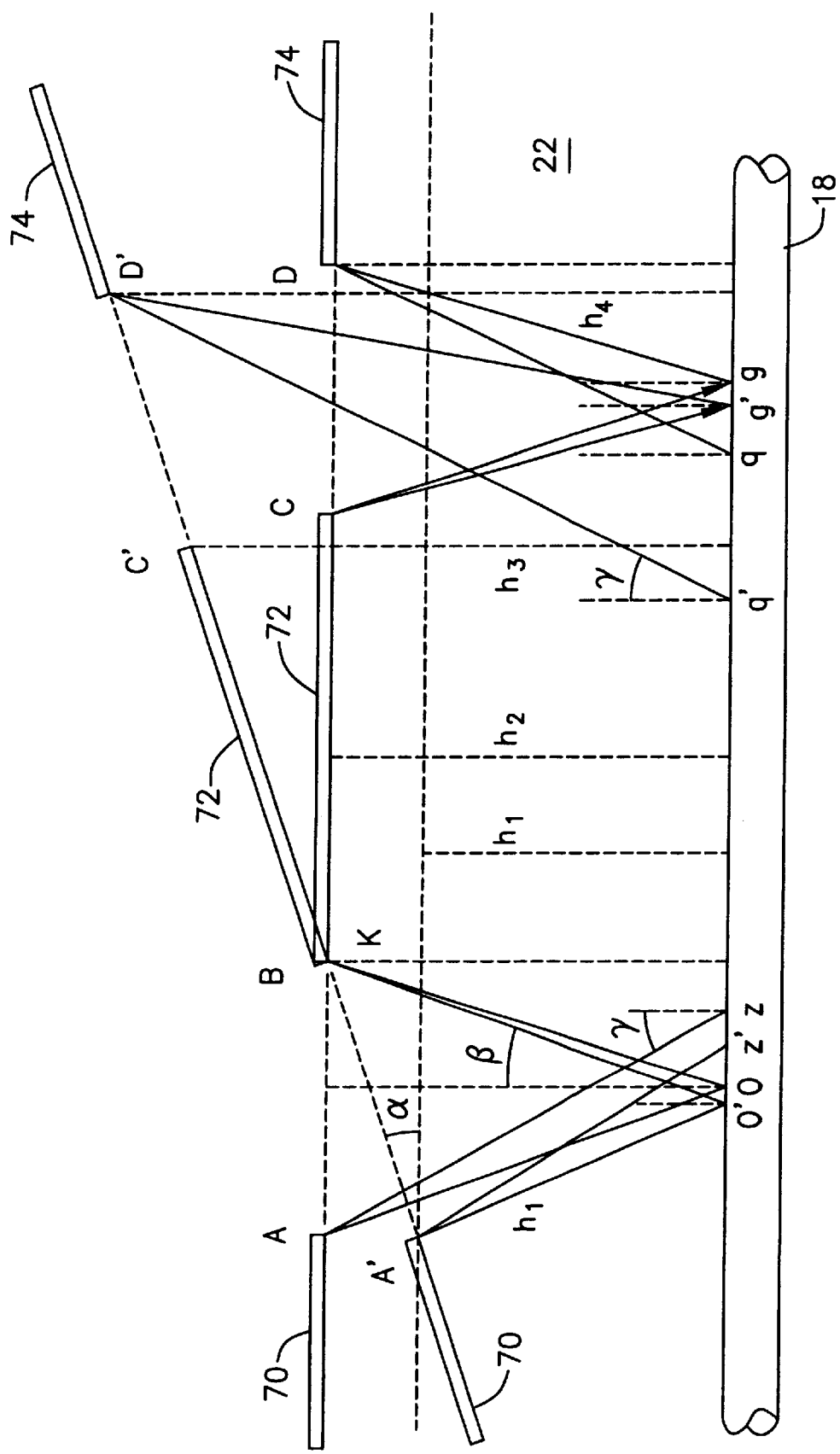
FIG. 4C shows the method of FIG. 4A as applied is cases of equal and unequal thicknesses of underlying tissue.

FIG. 4C shows the embodiment described hereinabove with respect to FIG. 4A in a manner which will facilitate the following mathematical discussion. The purpose of this discussion is to analyze the mathematics of acoustic velocity determination in greater detail.

FIG. 4C shows two possibilities, one in which the line connecting ultrasonic elements 70, 72 and 74 is parallel to bone 18 and, a second in which the line connecting ultrasonic elements 70, 72 and 74 is not parallel to bone 18. In each one of these cases the mathematical derivation of the ultrasonic bone velocity is different.

Figure 4D:
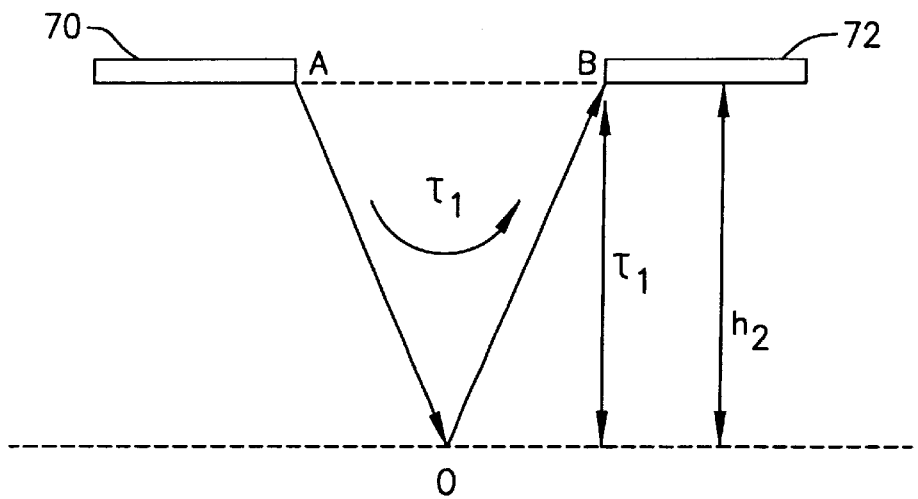
FIG. 4D is a simplified partial schematic of a portion of the method of FIG. 3.
Figure 4E:
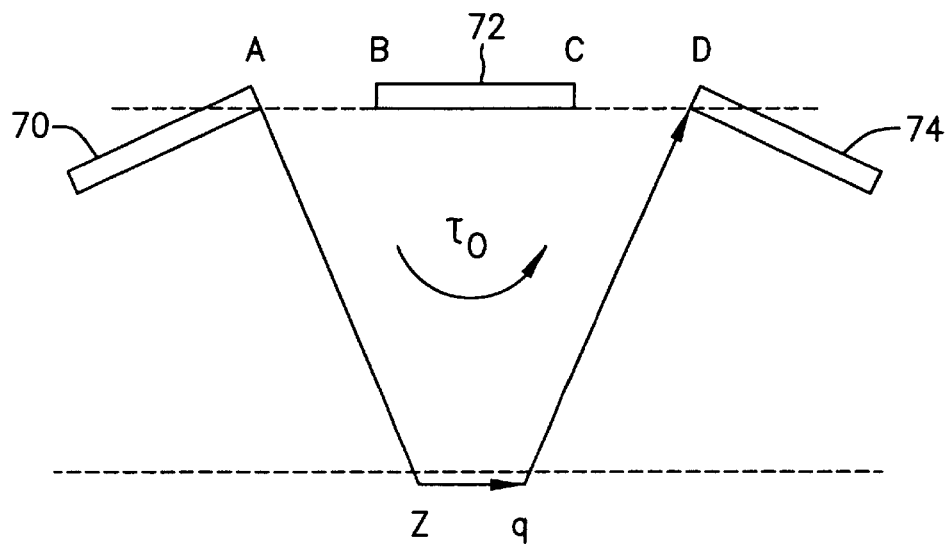
FIG. 4E is a simplified partial schematic of a portion of the method of FIG. 2.

FIGS. 4D and 4E show the times that are actually measured in the above described method. The equations which link these times to FIG. 4C, are as follows:

$$\tau_1 = \frac{AO + OB}{V_t} \tag{20}$$

$$\tau_2 = \frac{2h_2}{V_t} \tag{21}$$

$$\tau_3 = \frac{Cg + gD}{V_t} \tag{22}$$

$$\tau_0 = \frac{Az}{V_t} + \frac{zq}{V_B} + \frac{qD}{V_t} \tag{23}$$

In addition, $\gamma$ is the Brewster angle. As used in the following equations, "a" is equal to the distance between points A and B (AB), b=BC and c=CD. In addition, the letter A, when not referring to the point A, refers to the sum of a+b+c, i.e., the shortest distance between transmitter 70 and receiver 74.

In a first, simplified case, which rarely occurs in practical situations, the line connecting the ultrasonic elements 70, 72 and 74 is parallel to bone 18. Thus:

$$h_1 = h_2 = h_3 = h_4 \tag{24}$$

$$\sin\alpha = 0 \tag{25}$$

$$\tau_1 = \tau_3 \tag{26}$$

Soft tissue acoustic velocity V22 or $V_t$ is determined to be:

$$V_t = \frac{a}{\sqrt{\tau_1^2 - \tau_2^2}} \tag{27}$$

With bone acoustic velocity $V_{18}$ or $V_b$ determined by the following equation:

$$V_B^2 \times \left(\frac{\tau_0^2}{\tau_2^2} - 1\right) - V_B\left(2\frac{\tau_0}{\tau_2^2}A\right) + \left(\frac{A^2}{\tau_2^2} + V_t^2\right) = 0 \tag{28}$$

Solved as:

$$V_B = \frac{A}{\tau_0} \times \frac{1 \pm \frac{\tau_2}{\tau_0}\sqrt{1 - \frac{a^2}{A^2} \times \frac{\tau_0^2 - \tau_1^2}{\tau_1^2 - \tau_2^2}}}{1 - \frac{\tau_2^2}{\tau_0^2}} \tag{29}$$

It should be noted, that in order to determine the bone acoustic velocity using the above described equations, not only does $h_1 = h_2 = b_3 = h_4$ but also $\tau_1 = \tau_3$. Due to variations in the acoustic velocity in soft tissue, resulting from soft tissue non-uniformities, this is rarely the case in in vivo measurements. However, one of the above mentioned two conditions can usually be met. In a preferred embodiment of the invention, the sensor is embedded in a rocker device. Such a rocker device is described in U.S. Pat. No. 5,143,072, cited above. The rocker is rocked along an axis connecting transmitter 70 with transmitter/receiver 72 and receiver 74 and a plurality of measurements of soft tissue velocity and soft tissue thickness are performed. Bone velocity measurements are performed either when $h_1 = h_2 = h_3 = h_4$ or when $\tau_1 = \tau 3$.

A particular case in point is the acoustic velocity measurement of the femur. The surface geometry of the femur is not substantially flat in any portions thereof In addition, the thickness of the soft tissue overlying the femur is high, on the order of 6 cm The bone acoustic velocity measurements are preferably performed when transmitter 70 and receiver 74 are both the same distance from the femur, to minimize false reflections.

When the line connecting ultrasonic elements 70, 72 and 74 is not parallel to bone 18, the following, more complex equations must usually be solved to determine the bone acoustic velocity. In the following equations, it is assumed that the configuration is similar to that (non-parallel) configuration shown in FIG. 4C. If the configuration is a mirror image of that shown in FIG. 4C, $h_2$ should be measured at point C, and the equations modified accordingly.

Soft tissue acoustic velocity $V_{22}$ or $V_t$ is determined using the following equation:

$$V_t^4 \times \left[ (\tau_3^2 - \tau_2^2) + \frac{(\tau_1^2 - \tau_2^2) \times (2b + c)}{a} + \right. \tag{30}$$

$$\left. \frac{c^2 \times (\tau_1^2 - \tau_2^2)^2}{4\tau_2^2 a} - (2b + c)^2 \times \frac{(\tau_1^2 - \tau_2^2)^2}{4\tau_2^2 a^2} \right] +$$

$$V_t^2 \times \left[ \frac{(2b + c)^2 \times (\tau_1^2 - \tau_2^2)}{2\tau_2^2} - a \times (2b + c) - \frac{c^2 \times (\tau_1^2 - \tau_2^2)}{2\tau_2^2} - c^2 \right] +$$

$$\frac{a^2 c^2}{4\tau_2^2} - (2b + c)^2 \times \frac{a^2}{4\tau_2^2} = 0$$

Bone acoustic velocity is determined using an equation similar to equation (28):

$$p_1 V^4 B + p_2 V^3 B + p_3 V^2 B + p_4 V_B + p_5 = 0 \tag{31}$$

Where:

$$p_1 = \tau_0^2 - \left( \tau_2 + \frac{b + c - a}{V_t} \times \sin\alpha \right)^2 \tag{32}$$

$$p_2 = -2\tau_0 A \cos\alpha \tag{33}$$

$$p_3 = A^2 \cos^2\alpha - V_t^2 \times \left[ \tau_0^2 - 2\left( \tau_2 + \frac{b + c - a}{V_t} \times \sin\alpha \right)^2 \right] \tag{34}$$

$$p_4 = 2\tau_0 A V_t^2 \cos\alpha \tag{35}$$

$$p_5 = -V_t^2 \times [A^2 \cos^2\alpha + (V_t \tau_2 + (b + c - a) \times \sin\alpha)^2] \tag{36}$$

$$\sin\alpha = \frac{a^2 - V_t^2(\tau_1^2 - \tau_2^2))}{2 V_t \tau_2 a} \tag{37}$$

The exact length of the different path segments in bone 18 and in soft tissue 22 can be determined using the geometrical relationships shown in FIG. 4C and the abovedetermined soft tissue and bone velocity. In particular, the path of the wave from transmitter 70 to receiver 74 is:

$$z'q' = (a + b + c)\cos\alpha - \tau_2 V_t \frac{\sin\gamma}{\cos\gamma} - (b + c - a)\sin\alpha \frac{\sin\gamma}{\cos\gamma} \tag{38}$$

$$A'z' = \frac{\tau_2 V_t - 2a\sin\alpha}{2\cos\gamma} \tag{39}$$

$$D'q' = \frac{\frac{\tau_2 V_t}{2} + (b + c) \times \sin\alpha}{\cos\gamma} \tag{40}$$

Figure 5A:
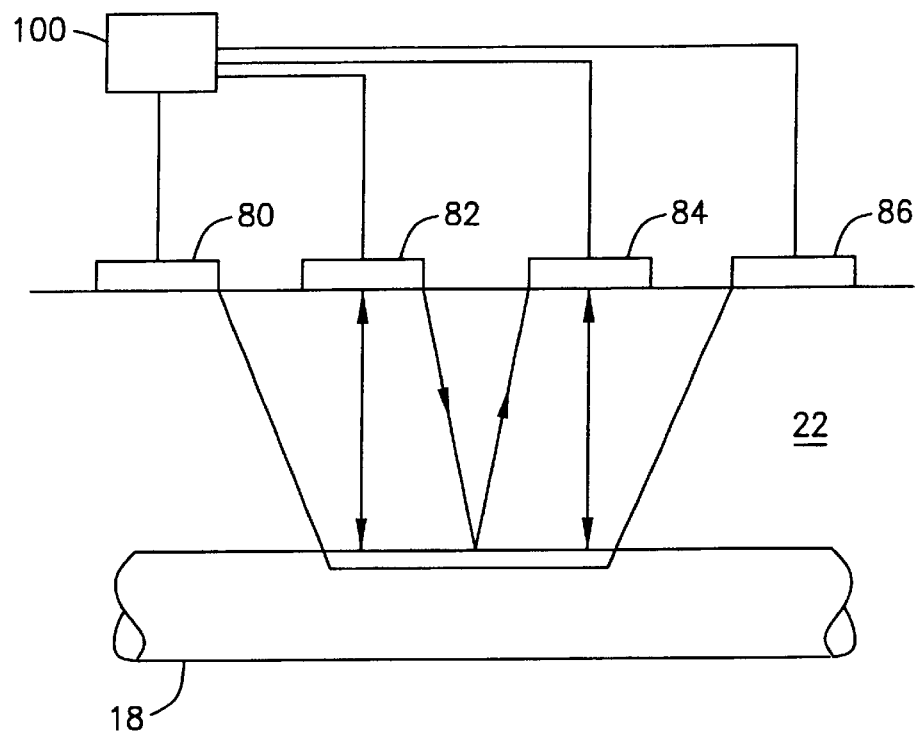
FIGS. 5A and 5B show a two step method of acoustic bone velocity measurement according to another preferred embodiment of the present invention.
Figure 5B:
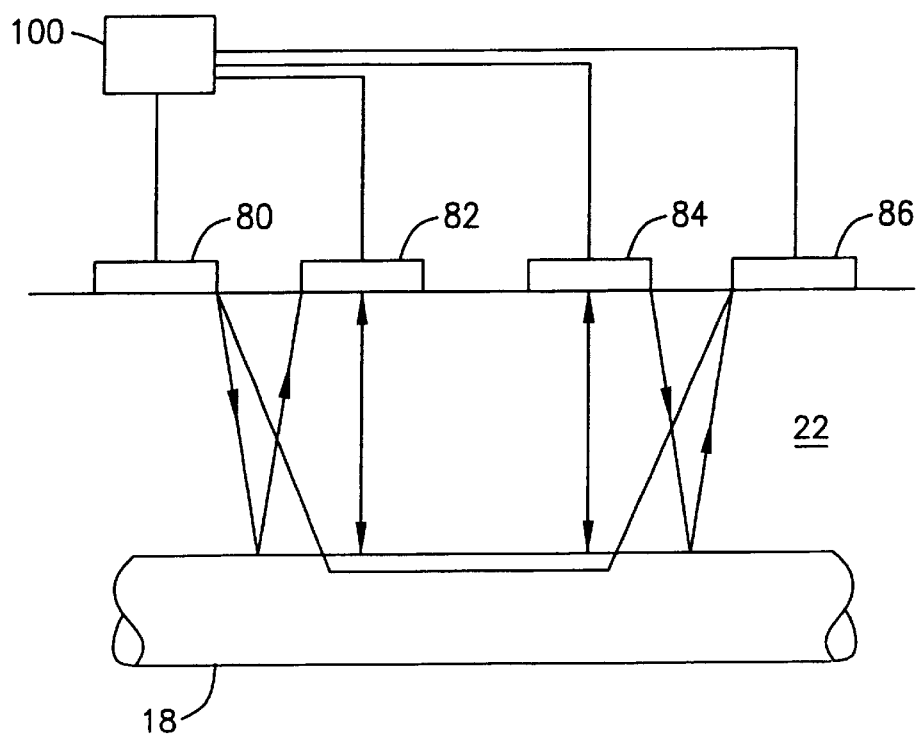

FIGS. 5A and 5B show an additional embodiment of the present invention. Acoustic bone velocity is measured using the above described method of measuring the travel time of a signal emitted by a transmitter 80 until it is first received by a receiver 86. However, this embodiment differs from the embodiment of FIGS. 4A and 4B in that a pair of transmitter/receivers 82 and 84 are used in place of the single transmitter/receiver 72. This change has two main benefits. First, the thickness of tissue 22 and the acoustic velocity in tissue 22 are measured in more than one location. Thus, body areas having uneven surfaces or varying acoustic soft tissue velocity are recognized. Preferably, the operator is alerted and he takes appropriate action, such as changing the measured location Alternatively, acoustic velocity calculations are corrected for these differences.

Second, transmitter/receiver 82 can be located independently of transmitter/receiver 84. In the embodiment of FIGS. 4A and 4B, a preferred situation was described wherein the path of the signals used for acoustic soft tissue velocity determination coincide with the path used for acoustic bone velocity determination. In the present embodiment, transmitter/receiver 82 can be positioned relative to transmitter 80 so that this preferred situation occurs (in the method described below with respect to FIG. 5B). Transmitter/receiver 84 is positioned in a similar manner relative to receiver 86. It should be noted that the distance between transmitter 80 and receiver 86 does not adversely effect the measurement in a substantial manner.

FIGS. 5A and 5B describe a two step process wherein some measurements are taken in the first step, and some in the second. However, the order of these steps does not matter and preferably the two steps are performed simultaneously using different frequencies or wave forms. If a two step method is used, the acoustic bone velocity determination is preferably performed in both steps.

However, performing only one of these two steps is sufficient in determining the bone acoustic velocity. Preferably, the decision which step to perform is made based on the configuration of transmitter/receiver 82, transmitter/receiver 84, transmitter 80, receiver 86 and bone 18, which affects the relative locations of the soft tissue velocity measurement and the bone velocity measurement.

In the step descried in FIG. 5A, acoustic bone velocity is measured by measuring the travel time of a signal between transmitter 80 and receiver 86. In addition the following measurements useful for soft tissue velocity determination are performed:

(a) the thickness of tissue 22 under transmitter/receiver 82;

(b) the thickness of tissue 22 under transmitter/receiver 84; and (c) the travel time of a signal from transmitter/receiver 82 to transmitter/receiver 84.

These measurements are sufficient for acoustic soft tissue velocity determination and for determination of changes in the thickness of tissue 22. It should be noted that if transmitter/receiver 82 and transmitter/receiver 84 are far enough apart such that a signal from tissue transmitter/receiver 82 to transmitter/receiver 84 passes through bone 18, tissue measurement (c) is not performed. However, measurements (c) and (d), performed in the step of FIG. 5B compensate for not making measurement (c).

In the step shown in FIG. 5B, acoustic bone velocity is measured by measuring the travel time of a signal between transmitter 80 and receiver 86. In addition the following measurements tissue useful for soft tissue velocity determination are performed:

(a) the thickness of tissue 22 under transmitter/receiver 82;

(b) the thickness of tissue 22 under transmitter/receiver 84;

(c) the travel time of a signal from transmitter 80 to transmitter/receiver 82; and (d) the travel time of a signal from transmitter/receiver 84 to receiver 86.

These measurements are sufficient for acoustic soft tissue velocity determination and for determination of changes in the thickness of tissue 22. Again, if the fastest path for a signal from transmitter 80 to transmitter/receiver 82 or from transmitter/receiver 84 to receiver 86 is through bone 18, measurement (c) and/or (d) are not performed. However, measurement (c) performed in the step of FIG. 5A compensates for these missed measurements.

It should be noted that the measurements performed in the step shown in FIG. 5B determine the acoustic soft tissue velocity in local regions surrounding the regions wherein the signal used for acoustic bone velocity determination travels. Thus, this embodiment is suitable for acoustic bone velocity determination in cases where the surface is known to be uneven or acoustic soft tissue velocity is known to vary. In addition, acoustic bone velocity determination is possible in over curved body parts, such as along a transverse axis of bone 18, due to the short path segment necessary along bone 18.

The small dimensions of the minimally required bone path segment make it possible to scan with a high spatial resolution, using embodiments of the present invention. For ample, to measure the acoustic velocity in a portion of the cortex of a tooth, a 10 MHz ultrasonic pulse can be used. Due to the high frequency of the ultrasound, the sensor dimensions can be in the order of 3 millimeters and the resolution better than 1 millimeters.

Figure 6A:
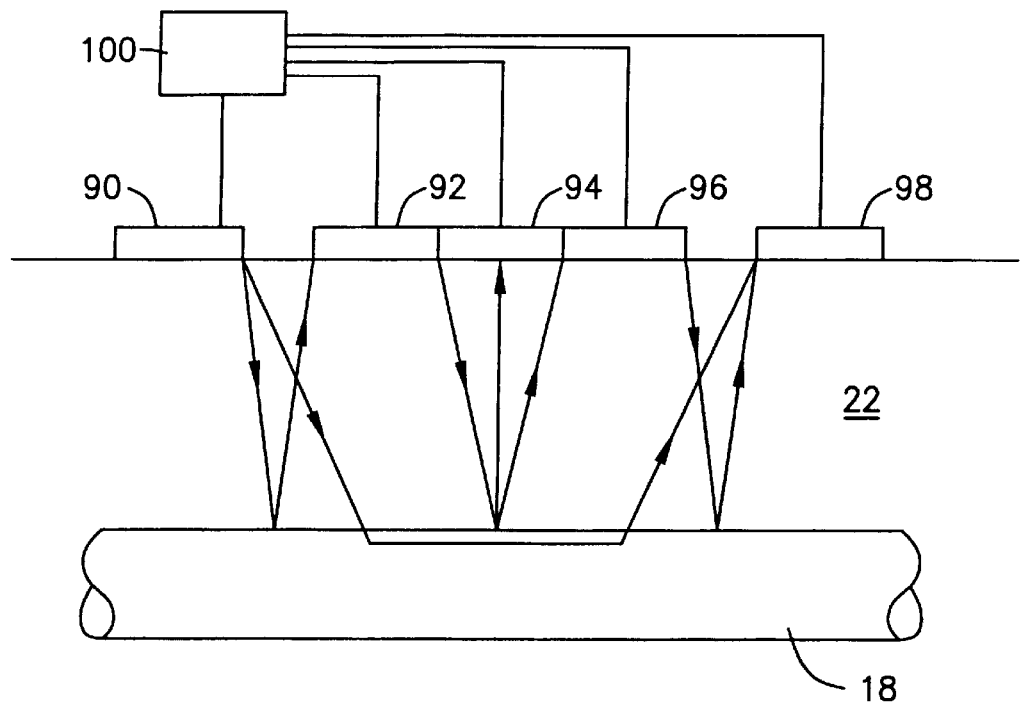
FIGS. 6A and 6B show a two step method of acoustic bone velocity measurement according to yet another preferred embodiment of the present invention.
Figure 6B:
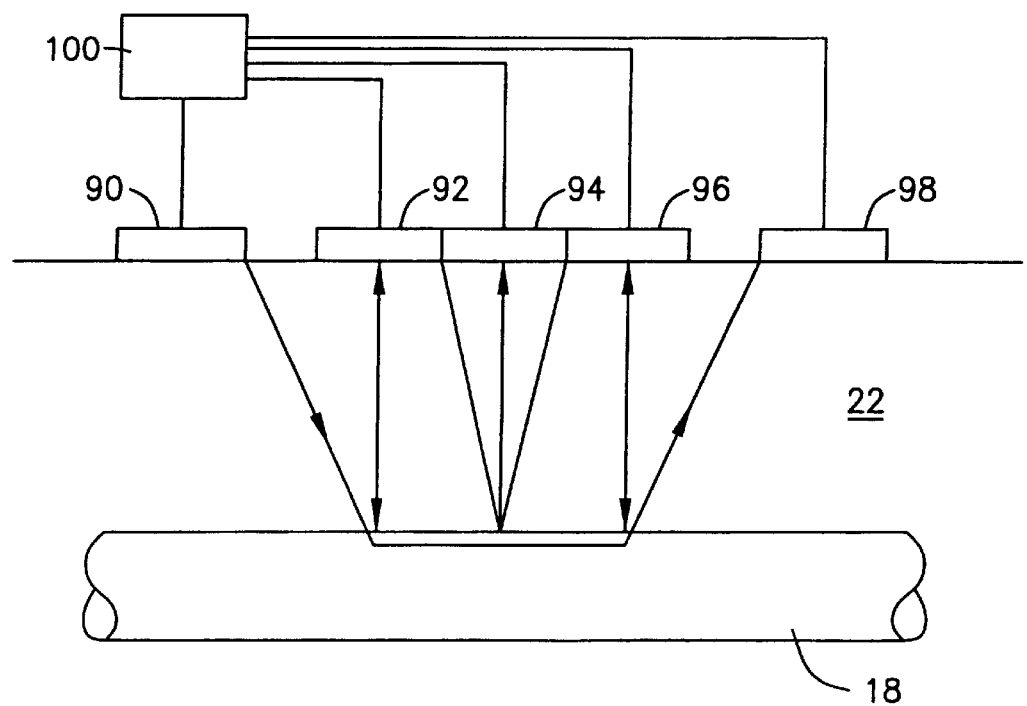

FIGS. 6A and 6B show another preferred embodiment using three transmitter/receivers, a transmitter and a receiver. As before, acoustic bone velocity is determined by measuring the travel time of a signal emitted by a transmitter 90 to a receiver 98. A two step process of acoustic soft tissue velocity determination is preferred.

FIG. 6A shows a first step, wherein the following measurements are performed:

(a) transmission time from transmitter 90 to a transmitter/receiver 92;

(b) transmission time from transmitter/receiver 92 to a transmitter/receiver 96;

(c) transmission time from transmitter/receiver 96 to receiver 98;

(d) the thickness of tissue 22 underlying a transmitter/receiver 94; and (e) transmission time from transmitter 90 tissue to receiver 98.

FIG. 6B shows a second step, wherein the following measurements are performed:

(a) transmission time from transmitter/receiver 92 to transmitter/receiver 96;

(b) the thickness of tissue 22 underlying transmitter/receiver 92;

(c) the thickness of tissue 22 underlying transmitter/receiver 94;

(d) the thickness of tissue 22 tissue underlying transmitter/receiver 96; tissue and (e) transmission time from transmitter 90 to receiver 98. Thus, the thickness of tissue 22 is measured at three locations so that changes in the thickness of tissue 22 are easier to incorporate in the calculation.

Preferably, transmitter/receivers 92 and 96 are arranged so that they measure the thickness of tissue 22 at the exact point wherein it is estimated that the acoustic bone velocity determination signal enters and leaves the bone. Transmitter/receiver 94 is preferably arranged so that it measures the thickness of tissue 22 at the estimated point of reflections for signals from transmitter/receiver 92 transmitter/receiver 96. Thus, a more precise estimate of the signal path length in tissue 22 is possible.

Figure 7A:
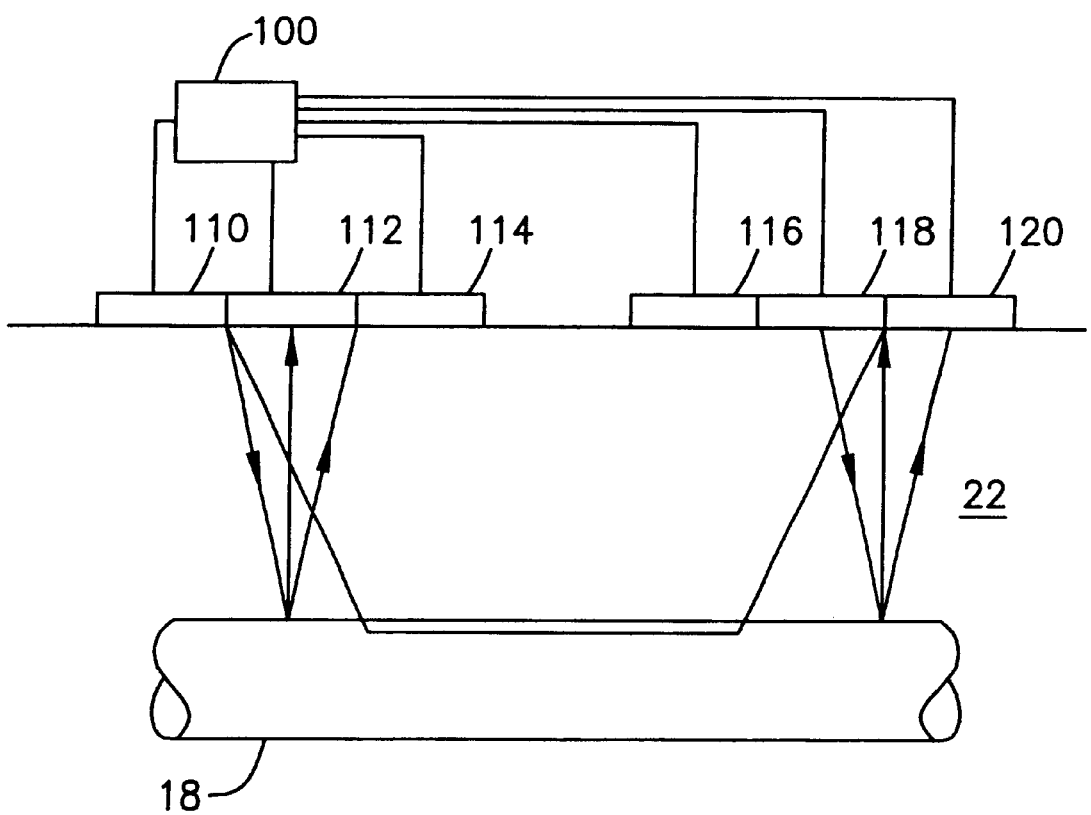
FIG. 7A shows yet another method of acoustic bone velocity determination according to another preferred embodiment of the present invention.
Figure 7B:
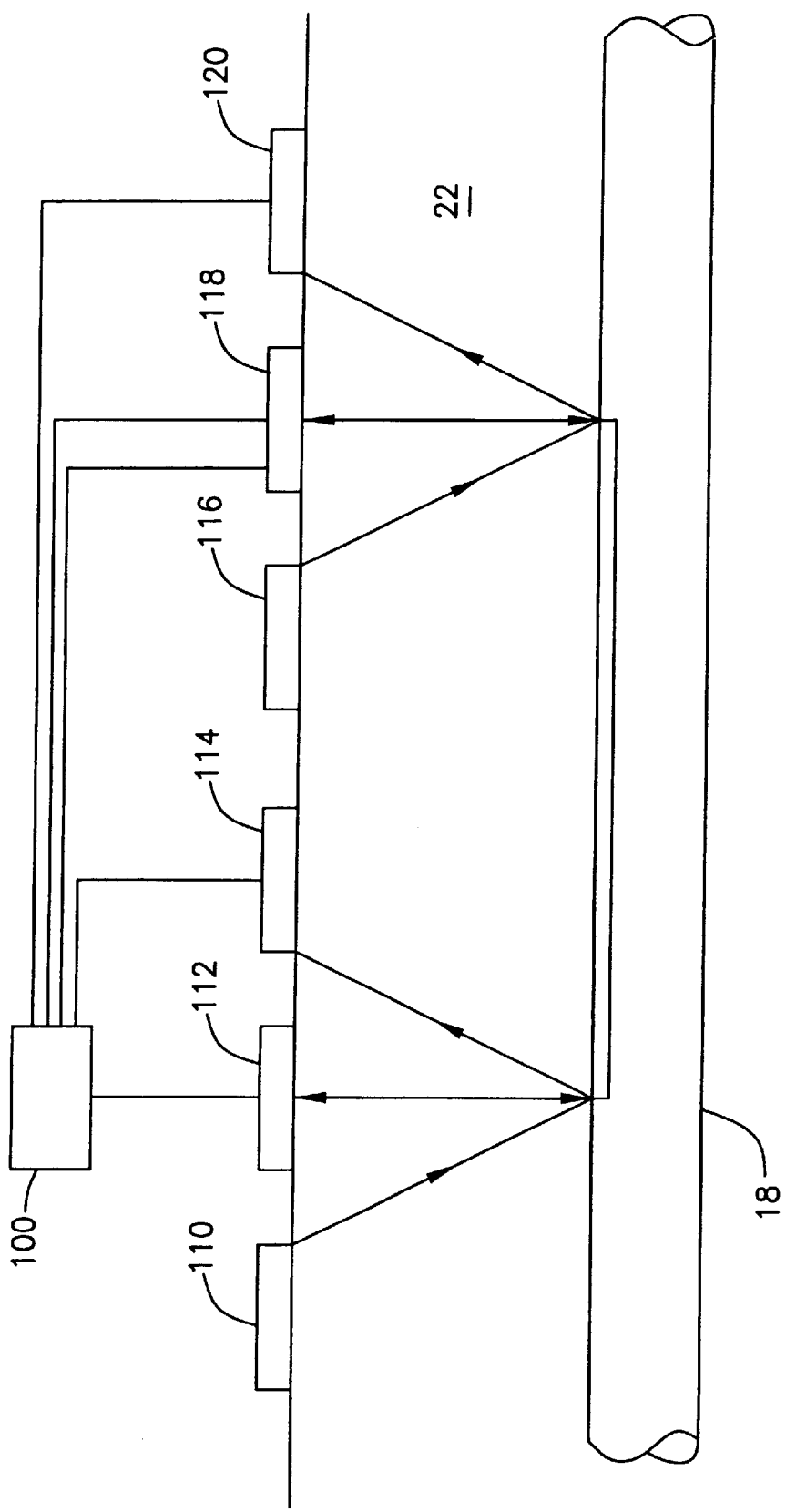
FIG. 7B shows an idealized version of FIG. 7A.

FIGS. 7A and 7B show yet another preferred embodiment of the present invention. As before, bone acoustic velocity is determined by measuring the travel time of a signal from a transmitter 110 to a receiver 120. However, a plurality of four transmitter/receivers 112, 114, 116 and 118 are used to measure the soft tissue acoustic velocity. This embodiment incorporates several features described in previous embodiments, and specifically shown in FIG. 7B:

(a) soft tissue acoustic velocity is determined separately for each area where the signal travels through tissue 22;

(b) the thickness of tissue 22 is measured at the point where the signal enters bone 18; and (c) the path of the signal coincides with the path used by signals for measuring the soft tissue acoustic velocity.

As can be appreciated, to achieve all of the above mentioned features, the transmitter/receivers are preferably located as shown in FIG. 7B and not as shown in FIG. 7A

Preferably two independent measurements processes are performed. A first process, performed in the region near transmitter 110 is:

(a) measuring the travel time for a signal from transmitter 110 to transmitter/receiver 114 (transmitter/receiver 114 need only be a receiver);

(b) measuring the thickness of tissue 22 underlying transmitter/receiver 112; and (c) calculating the thickness of tissue 22 and its acoustic velocity in the region near transmitter 110 using (a) and (b).

The second process is very similar, and is performed in the region near receiver 120:

(a) measuring the travel time for a signal from transmitter/receiver 116 tissue to receiver 120 (transmitter/receiver 116 need only be a transmitter);

(b) measuring the thickness of tissue 22 underlying transmitter/receiver 118; and (c) calculating the thickness of tissue 22 and its acoustic velocity in the region near receiver 120 using (a) and (b).

In the embodiments shown in FIGS. 4A–7B, all the ultrasonic elements are preferably collinear. However, the correct acoustic velocities can be determined if the ultrasonic elements are not collinear but the distances between the acoustic elements are known.

In the above described embodiments, a transmitter/receiver, such as transmitter/receiver 82 (FIG. 5A), both transmits and receives an ultrasonic wave. The inventor has found that the reception quality of an ultrasonic transmitter receiver is degraded for a short time after transmitting an ultrasonic wave. The measured received signal is the sum of the actual received signal and a transmission signal residue. This degradation can be prevented by separating transmitter/receivers into a pair of a transmitter and a receiver.

Figure 8A:
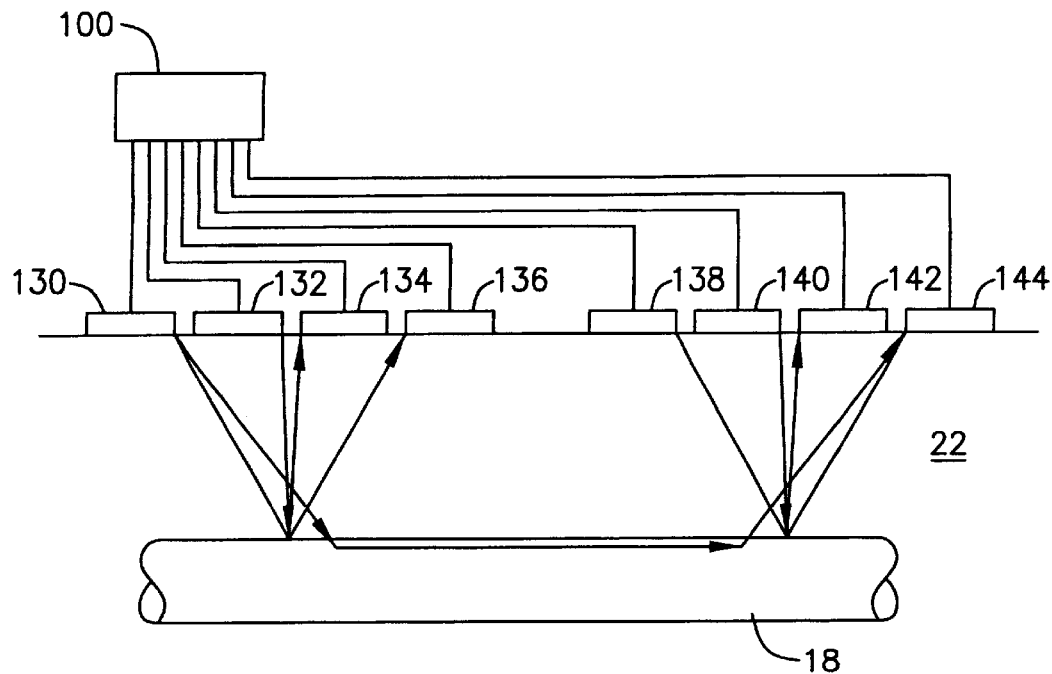
FIGS. 8A and 8B show preferred alternative versions of the methods shown in FIGS. 7A and 7B.
Figure 8B:
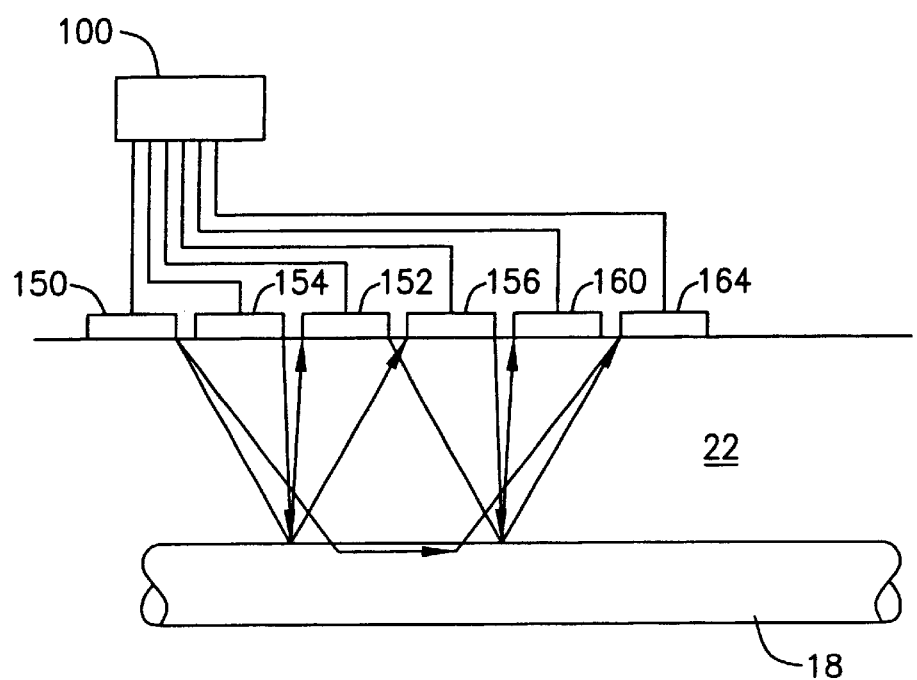

FIGS. 8A and 8B shows such a separation performed on the embodiments shown in FIGS. 7A and 7B. In FIG. 8A, a transmitter 130 corresponds to transmitter 110 (in FIG. 7A), a transmitter 132 and a receiver 134 correspond to transmitter/receiver 112, a receiver 136 corresponds to receiver 114, a transmitter 138 corresponds to transmitter 116, a transmitter 140 and a receiver 142 correspond to transmitter/receiver 118 and a receiver 144 corresponds to receiver 120. The method of operation is as described above in reference to FIG. 7A, excepting the thickness underneath transmitter/receiver 112 and 118 which are measured using a transmitter and a receiver instead of a transmitter/receiver. Measuring the thickness of soft tissue 22 using a transmitter and a receiver is as accurate as when using a single transmitter/receiver because the distance between the transmitter and the receiver (i.e., the distance between transmitter 132 and receiver 134) is much shorter than the thickness of soft tissue 22. In addition, the surface of bone 18 is sometimes irregular. When the reflection point of the wave from transmitter 112 is different from that of the wave from transmitter 110 to receiver 114, due to these irregularities, the soft tissue velocity determination is incorrect. The wave from transmitter 132 to receiver 134 travels at an angle, thus, the irregularities have a smaller effect on the reflection point.

FIG. 8B shows another alternative measuring method wherein transmitter/receivers are used, however, there is a large time differential between the transmitting and the receiving, so the reception quality is not degraded.

For the configuration of FIG. 8B a plurality of measurement steps are performed, including:

(a) measuring the signal propagation time from a transmitter 150 to a transmitter/receiver 156;

(b) measuring the signal propagation time from a transmitter/receiver 152 to a receiver 164;

(c) measuring the signal propagation time from a transmitter 154 to transmitter/receiver 152;

(d) measuring the signal propagation time from transmitter/receiver 156 to receiver 160; tissue and;

(e) measuring the wave propagation time between transmitter 150 and receiver 164.

The acoustic bone velocity of bone 18 is determined as described hereinabove. It should appreciated that the measurement steps may be performed simultaneously, however, preferably, transmitter/receivers do not transmit waves shortly before they are supposed to receive waves.

Acoustic bone velocity measurement has many uses. A first use is finding fractures and trains in bones. When a bone is overstressed or fractured (even a hairline fracture which is hard to see in X-ray images), its acoustic velocity changes markedly at the locations surrounding the fracture. Owing to the high resolution of some embodiments of the present invention, fractures in the wrist bones can also be identified, wherein the prior art devices are not capable of such discrimination.

A second use is estimating the density of the bone and portions thereof to determine the loss of minerals in the bone due to diseases of the bone, osteoporosis or low-gravity environments. It should be noted that the velocity is dependent mainly on Young's Modulus, i.e., the lower the velocity, the weaker the bone.

A third use is to chart the healing process of a broken bone. The common practice today is to keep the damaged bone in a cast until a predetermined period of time has elapsed. However, some patients require a longer or shorter healing period. X-ray images do not usually show enough detail to evaluate the integrity of the bone. By measuring and charting changes in acoustic bone velocity, a physician can more accurately estimate the state of bone repair. In a preferred embodiment, a small hole is drilled in the cast and the acoustic bone velocity is measured without removing the cast. In some patients it is advantageous to compare changes in acoustic bone velocities of opposing limbs.

Figure 9:
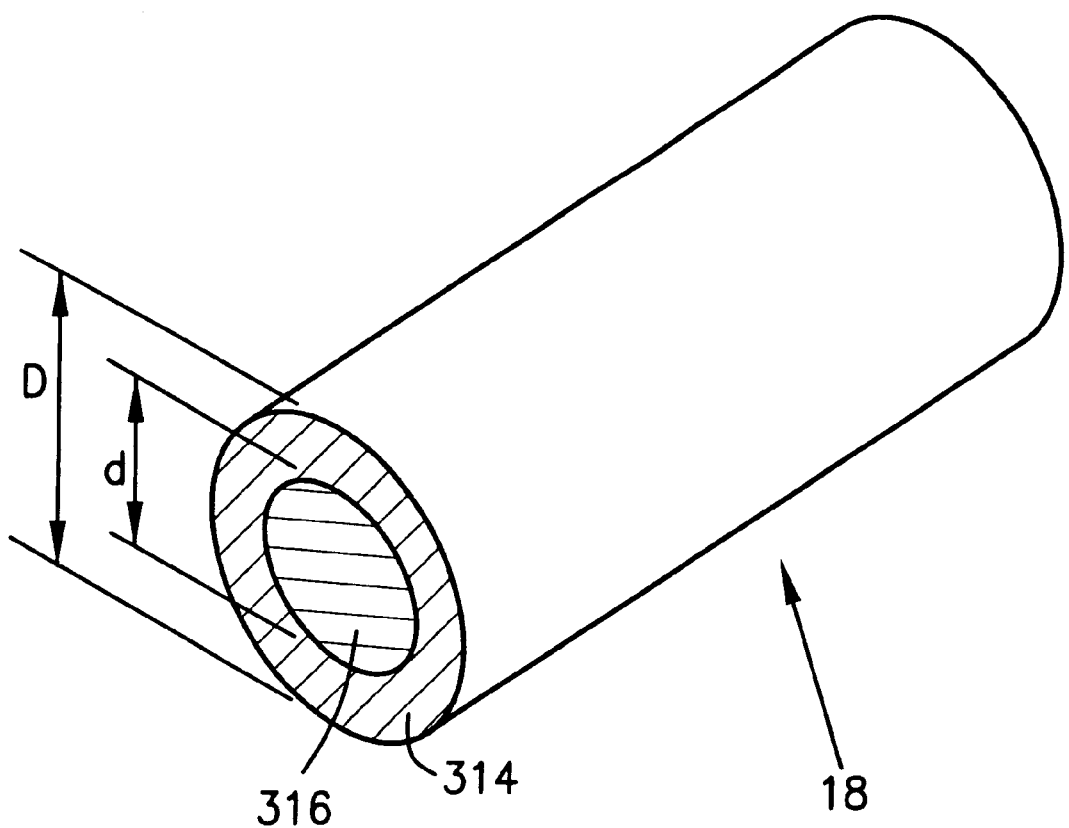
FIG. 9 is a partial schematic view of a cut human bone.

A fourth use of the invention is measuring the thickness of the cortex of the bone. FIG. 9 shows bone 18 having an inner core 316 and a cortex 314. The general diameter of bone 18 is D and the diameter of inner core 316 is d. Thus, the thickness of cortex 314 is (D−d)/2.

Figure 10:
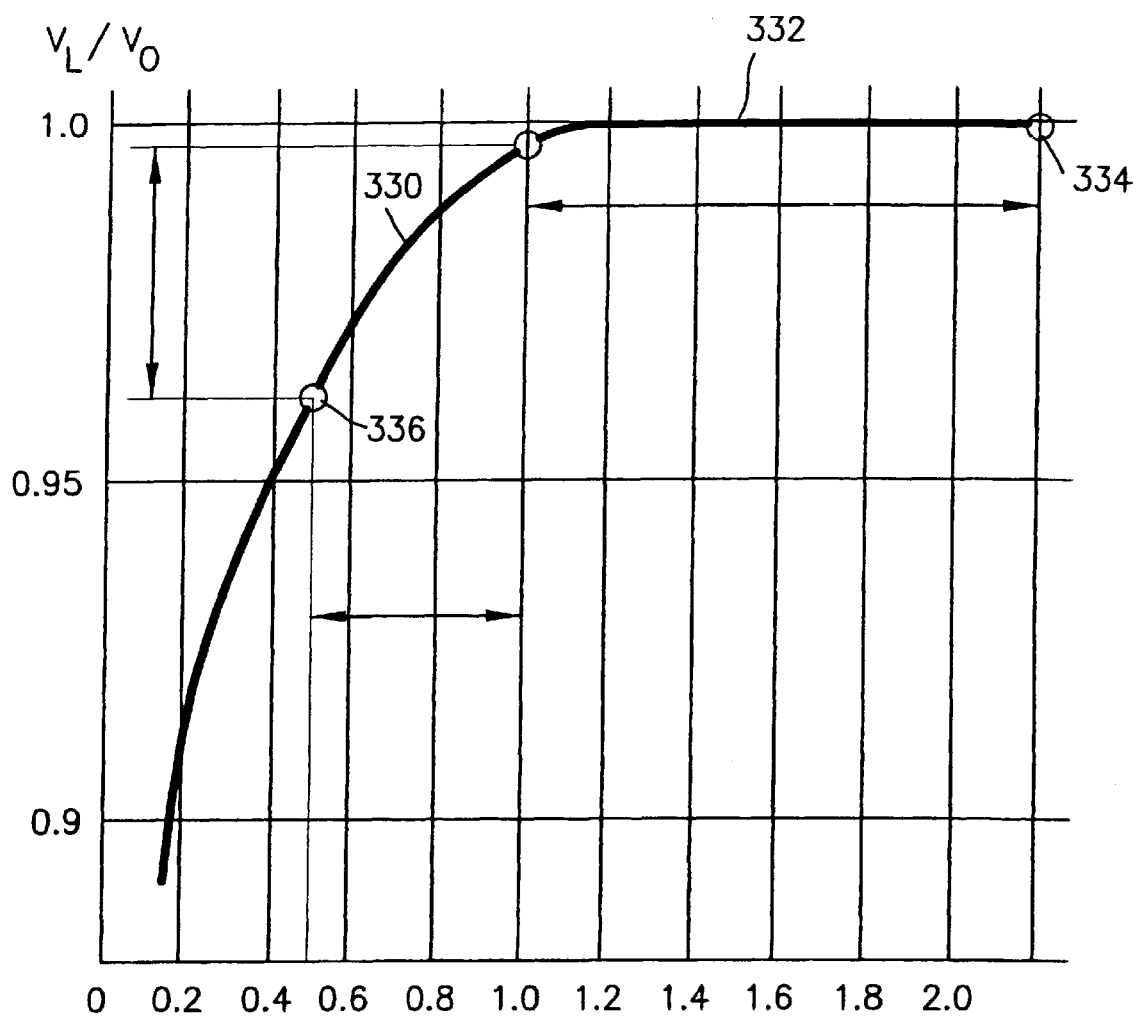
FIG. 10 is a graph showing the relationship between the thickness of an object and the velocity of an ultrasonic wave along its surface.

In accordance with a further embodiment of the present invention, control unit 100 estimates the thickness of cortex 314 through utilization of an theoretically-derived and empirically-validated, non-dimensional curve of normalized velocity vs. normalized thickness, as shown in FIG. 10 to which reference is now made. A discussion of the creation of the curve in FIG. 10 is discussed in the book, *Stress Waves in Solids*. written by H. Kolsky, Oxford and Clarendon Press, 1953.

The precise shape of the curve varies with the type of material being measured. However, it is has been determined by the present inventors that the shape of the curve is approximately constant for human bones.

The velocity $V_L$ in the curve of FIG. 10 is normalized by the velocity $V_O$ that would be achieved in an infinite solid and the thickness is normalized by the wavelength, $\lambda$, of the signal from the transmitter 70. $\lambda$ is, of course, determined by $V_{18}$:

$$\lambda = V_{18}/f \qquad (61)$$

where f is the frequency of the ultrasound signal. It has been determined by the inventors that the curve is approximately the same whether the thickness is the thickness D (FIG. 9) of bone 18 tissue or it the thickness (D−d)/2 (FIG. 9) of cortex 314. The proposed explanation is that the when the cortex is thick relative to $\lambda$, the inner portions of the bone have no effect on the acoustic velocity. However, when the cortex is thin relative to $\lambda$, the inner portions of the bone affect the acoustic velocity. The inner portions of bones are usually much softer than the cortex, so their acoustic velocity is much lower than the cortex's acoustic velocity. Thus, if a higher frequency is used, a thinner bone can be measured.

It is noted that the curve has a region 330, for relatively small velocity ratios and small diameter/wavelength ratios and a region 332 for diameter/wavelength ratios greater than about 1.5 which is asymptotic to 1.0.

To estimate the thickness (D−d)/2 for a bone 18, transmitter 70 is operated twice, once with a high frequency input signal and once with a low frequency input signal. For each measurement, control unit 100 operates, as described hereinabove with respect to FIGS. 4A and 4B, to determine the received velocity. Alternatively, in a preferred embodiment of the present invention transmitter 70 is a broadband transmitter and is operated only once. In addition, control unit 100 comprises frequency filters for separating received high frequency signals from low frequency signals. Thus, the high frequency velocity and the low frequency velocity are, simultaneously measured.

The response to the high frequency input signal, which has a low wavelength $\lambda$ provides a velocity data point 334 somewhere along the region 332 from which the velocity $V_O$ can be determined. The precise location of data point 334 is unknown, since the thickness is not yet determined. However, it is unimportant.

The response to the low frequency input signal provides a velocity data point 336 somewhere within the region 330. Because the velocity $V_L$ is known from the measurement and the velocity $V_O$ is known from the previous measurement, the location on the curve of the data point 336 is known. Therefore, the ratio (D−d)/(2*$\lambda$) can be determined. Since $\lambda$ is known from the frequency of the transmitter 70 and the known velocities, the thickness of cortex 314 (D−d)/2 can be determined.

It should be appreciated that the above described fourth use is more practical when using the instant method of acoustic bone velocity determination, than when using prior art methods. High frequency signals attenuate rapidly when traveling through bone material. So, only when the path in bone 18 is short, as is possible using the present invention, are high is frequency ultrasonic waves practical. Thus, in a preferred embodiment of the invention, the high frequency input signal used is higher than in the prior art and therefore, suitable for thinner bones.

It should be noted that the above described method of emitting a single broadband signal instead of two frequency specific signals is applicable to prior art methods of bone thickness determination, such as the methods shown in U.S. Pat. No. 5,143,072.

Figure 11:
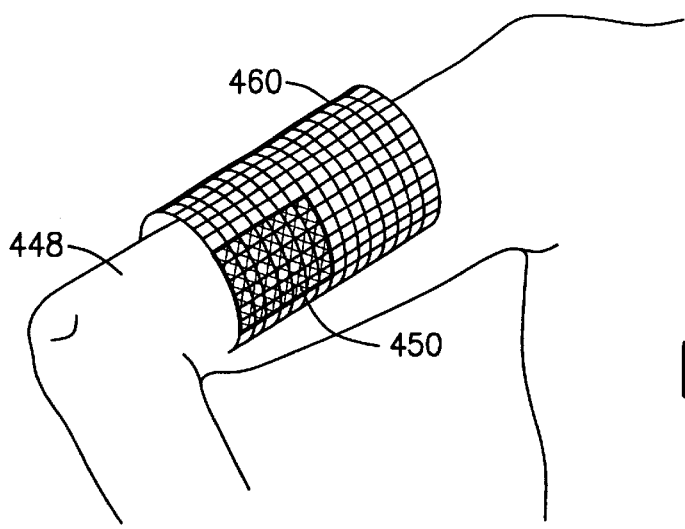
FIG. 11 is a schematic illustration of an alternative embodiment of the present invention utilizing an array of piezoelectric transducers.
Figure 12:
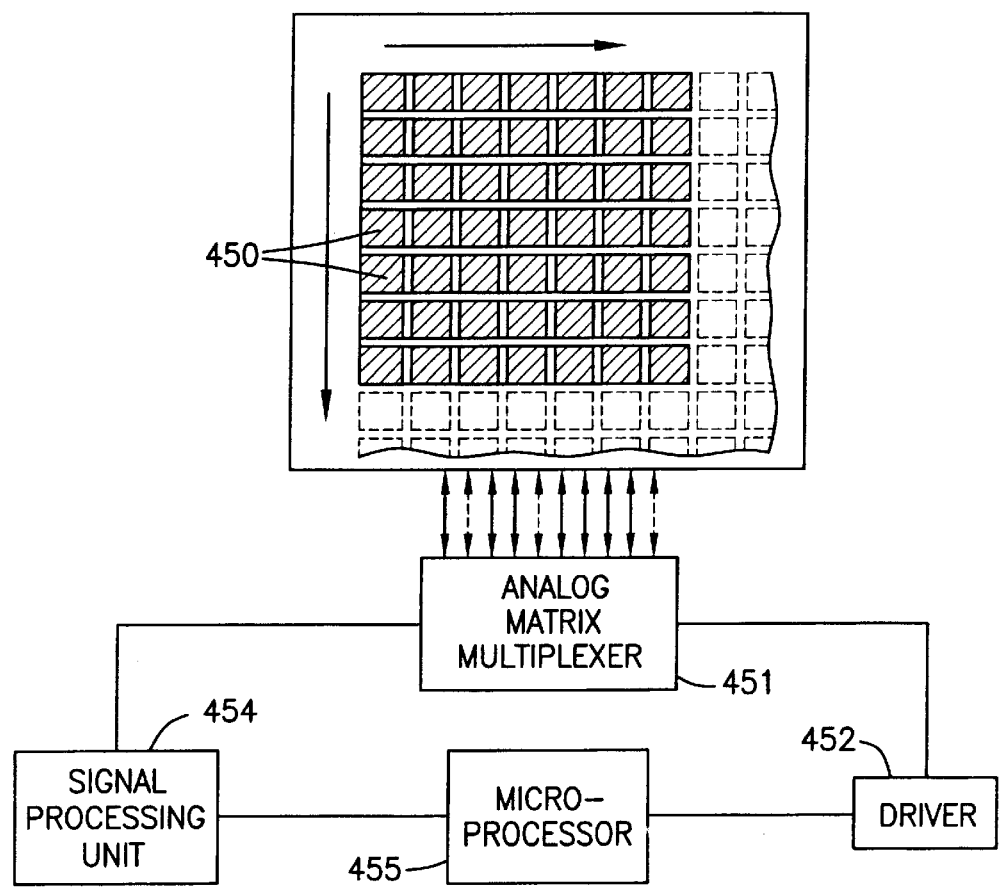
FIG. 12 is a schematic illustration of the array of FIG. 11, illustrating the connections of the traducers to control and signal processing elements.

Reference is now made to FIGS. 11 and 12 which illustrate aspects of a further embodiment useful for scanning across a section 448 of a human body, such as an arm.

In this embodiment, a sensor device formed of an array of ultrasonic transmitter/receiver cells 450 is placed onto or wrapped around section 448 or is formed into a sock-like element 460. The cells of array 450 are preferably formed from a piezoelectric material such as a piezo-ceramic. Array 450 is typically acoustically coupled to section 448 in a standard manner.

Typically, as shown in FIG. 12, the input and output wires of each cell of array 450 are connected to an analog matrix multiplexer 451 which, in turn, is connected to a driver 452 and to a signal processing unit 454. Driver 452 and unit 454 are typically controlled via a microprocessor 455.

Multiplexer 451 enables each cell of array 450 to be individually accessed and is operative to define each cell as a receiver, a transmitter, a transmitter-receiver or as non-active.

The cells of array 450 may be individually too small to form ultrasonic transducers for use in prior art methods, due to the attenuation caused by long paths through bone 18. Therefore, a plurality of groups of cells of array 450 in desired locations were electronically and selectably defined to be the ultrasonic elements. In a preferred embodiment of the present invention, each cell of array 450 is a separate ultrasonic element as described herein. Alternatively, groups of cells are defined as transducers, as shown in the prior art. However, one of the operation modes described below is preferably used.

A first preferred method of operation is to select cells and groups of cells that approximate the functionality of the embodiments described hereinabove. Thus, optimal placement of transmitter/receivers can be achieved without moving ultrasonic elements.

In a preferred embodiment of the invention, a two step method is used to determine the configuration of array 450 as transmitters and receivers. As described hereinabove, a preferred embodiment of the invention uses sensors which are optimized for a specific soft tissue thickness between the sensor and bone 18. Using array 450 to image bone 18 it is possible to determine the thickness of underlying soft tissue 22, before bone velocity determination:

(a) determining the thickness of underlying soft tissue 22; and (b) configuring array 450 into transmitters, receivers and transmitter/receivers having optimal distances therebetween, which are calculated based on the determined thickness of soft tissue 22.

Alternatively, an ultrasonic sensor comprises one or more transmitters and/or receiver and a cell array. The cell array is configured to be used in place of some, but not all of the ultrasonic elements described in the embodiments hereinabove. For example, in the embodiment of FIG. 5A, transmitter/receivers 82 and 84 can be emulated by a cell array.

A second preferred method of operation maps bones and soft tissues by operating different cells of array 450 instead of moving a unit comprising a plurality of ultrasonic units. Thus, the bone velocity at different positions and in different directions can be measured without physically moving the apparatus.

It should be noted that many prior art methods of bone acoustic velocity determination use an inexact estimate for the values of soft tissue thickness and soft tissue velocity. If an embodiment of the present invention is used to determine more accurate values for the soft tissue thickness and velocity, these prior art methods will give more precise results.

In addition, measurement of soft tissue velocity is useful for determination of water, fat and muscle content of the tissue. Thus, dehydration and rehydration of a patient can be analyzed by measuring the soft tissue velocity, in a selected part of the patient's body, over a period of time. The muscle/fat ratio of the tissue can be determined if the water content of the tissue is known, or by averaging several results taken before and after the patient drinks water.

When scanning a human female breast the air tissue boundary can be used as a reflection plane. Preferably the breast is urged against a resilient form so that it does not move during imaging.

In a preferred embodiment of the present invention, scanning is accomplished using a cell array as described hereinabove. Preferably, the scans include scans of the same soft tissue from multiple directions so that a velocity image of the tissue can be reconstructed, preferably using tomographic methods.

Figure 13A:
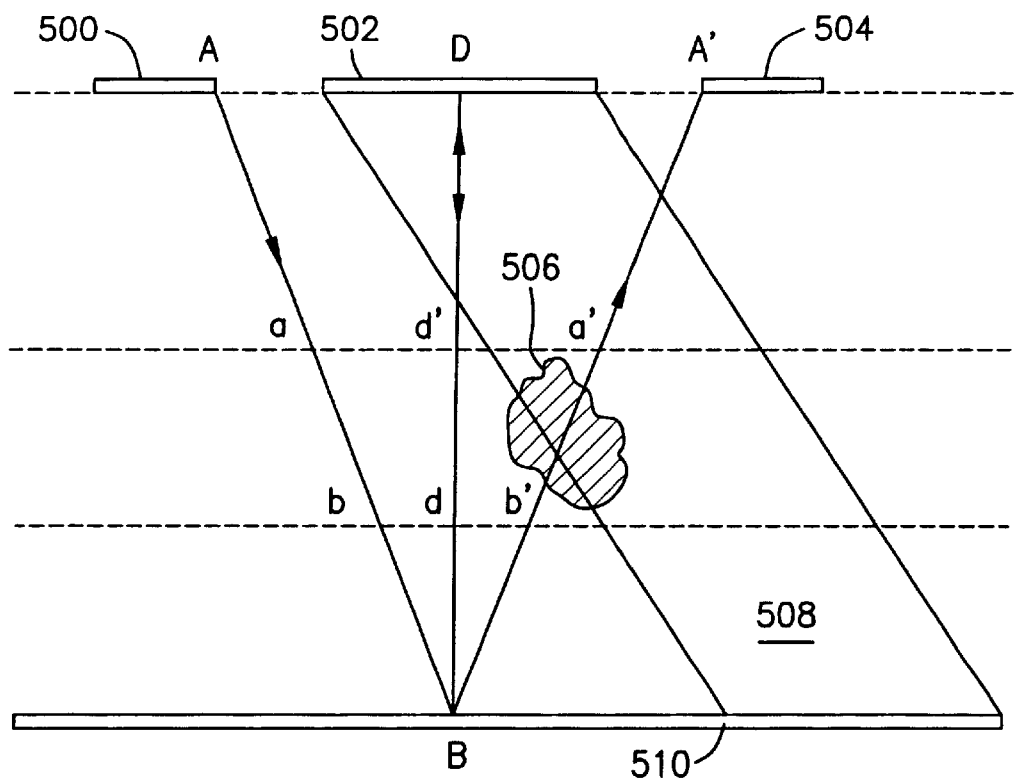
FIGS. 13A and 13B show a method of soft tissue analysis according to a preferred embodiment of the present invention.
Figure 13B:
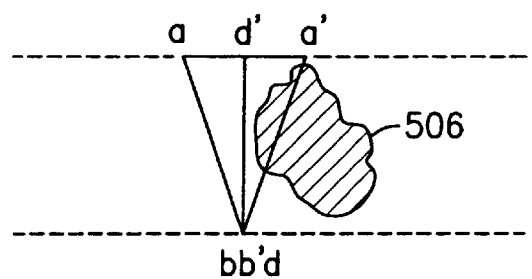

FIGS. 13A and 13B show a preferred embodiment of the invention related to soft tissue imaging. FIG. 13A shows a general soft tissue portion 508 which contains a soft tissue portion 506 which has a substantially different acoustic velocity. An example of such tissues is a human breast and a pathological neoplasm, such as a malignant tumor. The sensor used preferably comprises an array, of which a plurality of cells 502 comprise a scanner, as known in the art of ultrasound imaging. At least one cell comprises a transmitter 500 and at least one cell comprises a receiver 504. Scanner 502 scans tissue 508 until the location of tissue 506 is found (a scanning beam is shown by two parallel lines). Alternatively, tissue 506 is invisible using standard ultrasound imaging. In this case, the position of tissue 506 is preferably determined beforehand using another imaging method which also determines landmarks. These landmarks are found by scanner 502 and the position of tissue 506 is ascertained. The soft tissue velocity of tissue 508, in areas surrounding tissue 506 is determined using transmitter 500, receiver 504 and the plurality of cells which comprise scanner 502, using determination methods as described hereinabove. Then, the soft tissue velocity is determined in a manner which will force the path of the measurement wave to path through tissue 506. For example, if a cell grid is used, a plurality of soft tissue measurements are acquired and the measurements which are substantially different as assumed to have traveled through tissue 506.

FIG. 13B in conjunction with FIG. 13A shows a method of increasing the contrast between the measurement of the velocity in tissue 508 and the measurement of the velocity in tissue 506. The travel time in segments Aa, bB, Bd, Bb', Dd' and a'A' are constant and unaffected by the presence of tissue 506. These travel times can be determined beforehand in regions which do not include tissue 506. As a rest, the tissue velocity in tissue 506 can be better determined using only the segments ab, dd' and bVa'. Alternatively or additionally, knowledge of the approximate depth of tissue 506 can be used to increase the contrast in a similar manner.

Apparatus for soft tissue imaging can comprise as few as two transmitter/receivers, as described hereinabove with reference to soft tissue velocity determination methods. However, such apparatus preferably comprises a plurality of ultrasonic elements, preferably an array, such as array 450 (shown in FIG. 11). Alternatively, apparatus, as described hereinabove with reference to bone acoustic velocity determination, can also be used for soft tissue velocity determination. Typically in such cases, the bone traveling wave is either not transmitted, not received or not analyzed.

A single measurement in some preferred embodiments of the invention is only 2.5 milliseconds long, which is faster than most body rhythms. Several measurements taken along the course of a body rhythm can be used to measure the effect of the body rhythm on the measurement.

The above described embodiments are described in relation to a bone with surrounding soft tissue. However, a person skilled in the art will appreciate that these selfsame embodiments are just as useful for determining the mechanical properties of a general structure which is surrounded by layered material having a lower acoustic velocity. For example, metal braces which are encased in rubber.

As described hereinabove the acoustic velocities in a two layer structure are determined. It should be appreciated that the acoustic velocities in a multi-layer structure can be determined, providing that the layers are in a ascending order of acoustic velocity. For example, if a fast layer is covered with a slow layer and further covered with a very slow layer, the acoustic velocity of the very slow layer is first determined, then of the slow layer and then of the fast layer. Each determined velocity is used for determining the velocities in the next layer. However, if the slow layer and the fast layer are transposed, the slow layer is masked by the fast layer and the acoustic velocity of the slow layer cannot be determined.

Figure 14:
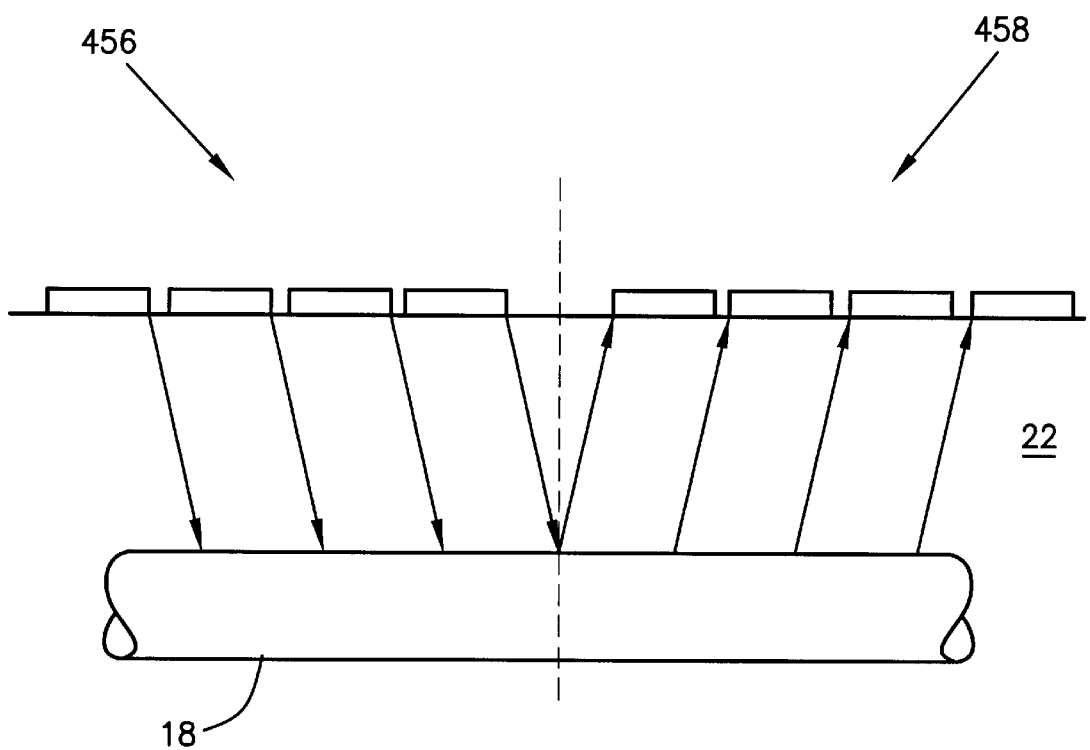
FIG. 14 shows a method of simultaneous bone-velocity determination and bone imaging according to a preferred embodiment of the present invention.

FIG. 14 shows an embodiment of the invention as used in conjunction with a scanning type ultrasonic sensor. A typical scanning ultrasonic sensor uses an array of cells, such as array 450, described above, to form a scanning beam, which scans a body portion, such as bone 18 and overlying soft tissue 22. In a preferred embodiment of the present invention, the acoustic bone velocity of bone 18 is determined concurrently with the scanning of bone 18. Thus, an image of bone 18 is acquired together with a map of the bone acoustic velocity, or bone strength, in the same area. A plurality of cells 456 form a scanning transmitter and a plurality of cells 458 form a receiver for imaging bone 18. The acoustic bone velocity is preferably determined between scanning pulses.

It will be appreciated by persons skilled in the art that the present invention is not limited by what has been particularly shown and described herein. Rather, the scope of the present invention is defined only by the claims which follow:

What is claimed is:

1. A method for determining, through an interposing medium having a first acoustic velocity, mechanical properties of a solid having a surface and having a second acoustic velocity, the method comprising:

transmitting a first ultrasonic wave along a transmission path from a first location through the interposing medium, along the surface and from the surface through the interposing medium to a second location, wherein the interposing medium comprises a biological tissue;

measuring a first travel time of the first wave along the transmission path;

determining the thickness of the interposing medium;

determining the first acoustic velocity; and calculating the second acoustic velocity utilizing the distance between the locations, the determined thickness of the interposing medium and the determined acoustic velocity in the interposing medium.

2. The method according to claim 1, comprising:

transmitting a second ultrasonic wave from a third location through the interposing medium to the surface;

measuring a second travel time of a portion of the second ultrasonic wave, the portion of the second ultrasonic wave being reflected off the surface to a fourth location;

transmitting a third ultrasonic wave from a fifth location through the interposing medium to the surface; and measuring a third travel time of a portion of the third ultrasonic wave, the portion of the third ultrasonic wave being reflected off the surface to the fifth location.

3. The method according to claim 2, comprising:

determining the first acoustic velocity utilizing the distance between the third and the fourth locations and the measured second and third travel times for the second and the third ultrasonic waves.

4. The method according to claim 3, wherein the first acoustic velocity is determined using the following equation:

$$V = D \div \sqrt{(T_1 + T_2)^2 - T_3^2}$$

wherein V is the first acoustic velocity, D is the distance between the third and the fourth locations, $T_1+T_2$ is the second travel time of the second wave and $T_3$ is the third travel time of the third ultrasonic wave.

5. The method according to claim 2, wherein determining the thickness comprising:

determining the thickness of the medium based on the distance between the third and the fourth locations and the measured second and third travel times for the second and third ultrasonic waves.

6. The method according to claim 2, wherein determining the thickness comprises:

determining the thickness based on the determined first acoustic velocity and the third travel time for the third ultrasonic wave.

7. The method according to claim 2, wherein the thickness is determined using the following equation:

$$H = V * T.$$

wherein V is the first acoustic velocity, T is the measured third travel time of the third ultrasonic wave and H is the thickness of the interposing medium.

8. The method according to claim 2, wherein a path of the second ultrasonic wave at least partially overlaps the transmission path of the first ultrasonic wave.

9. The method according to claim 2, wherein the thickness is determined at a point of intersection between the solid and the second ultrasonic wave.

10. The method according to claim 2, wherein the first and second ultrasonic waves are single frequency waves.

11. The method according to claim 2, wherein the first, second and third locations are located on a plane, and comprising:

rocking the plane relative to the surface boundary through a range of angles; and repeating a measurement of the first travel time at different rocking angles.

12. The method according to claim 11, wherein the measuring is performed when the distance between the first location and the surface is equal to a distance between the second location and the surface.

13. The method according to claim 11, wherein the acoustic velocity of the interposing medium underlying the first location and the second location is different.

14. The method according to claim 11, comprising determining a dependence of the acoustic velocity in the solid on the rocking angle.

15. The method according to claim 14, wherein the first, second and third locations are substantially collinear, and wherein the rocking comprises rocking the plane perpendicular to an axis collinear with the first, second and third locations.

16. The method according to claim 11, comprising determining a maximum determined acoustic velocity for the solid.

17. The method according to claim 11, comprising determining a minimum determined acoustic velocity for the solid.

18. The method according to claim 2, wherein the portion of the second ultrasonic wave and the portion of the third ultrasonic wave are reflected off substantially a same location on the surface.

19. The method according to claim 1, wherein the thickness is determined at a point of intersection between the first ultrasonic wave and the solid.

20. The method according to claim 1, wherein the solid comprises a biological tissue.

21. The method according to claim 20, wherein the solid comprises an in vivo bone.

22. The method according to claim 20, wherein the solid comprises a tooth.

23. The method according to claim 1, further comprising:
  (a) ultrasonically scanning a small part of the body portion containing the hard tissue;
  (b) determining the second acoustic velocity of the contained hard tissue from the results of (a); and
  (c) repeating (a) and (b) on at least a second part of the body portion to determine a map of velocities.

24. A method for measuring a first acoustic velocity of an interposing medium between a first location and a surface boundary with a further material, the method comprising:
  transmitting a first ultrasonic wave from the first location through the interposing medium to the boundary, wherein the interposing medium comprises a biological tissue;
  measuring a first travel time of a portion of the first ultrasonic wave, the portion of the first ultrasonic wave being reflected off the surface boundary to a second location;
  transmitting a second ultrasonic wave from a third location through the interposing medium to the boundary;
  measuring a second travel time of a portion of the second ultrasonic wave, the portion of the second ultrasonic wave being reflected off the surface boundary to the third location;
  determining the first acoustic velocity utilizing a distance between the first and the second locations and the measured first and second travel times for the first and second ultrasonic waves.

25. The method according to claim 24, wherein determining the first acoustic velocity comprises solving the following equation:

$$V = D \div \sqrt{(T_1 + T_2)^2 - T_3^2}$$

wherein V is the first acoustic velocity, D is the distance between the first and the second locations, $T_1+T_2$ is the measured first travel time of the first wave and $T_3$ is the measured second travel time of the second ultrasonic wave.

26. The method according to claim 24, wherein the interposed medium comprises a living tissue.

27. The method according to claim 24 wherein the first and second travel time are measured simultaneously.

28. The method according to claim 24, wherein a frequency of at least the first ultrasonic wave is at least 2 MHZ.

29. The method according to claim 24, wherein a frequency of at least the first ultrasonic wave is at least 5 MHZ.

30. The method according to claim 24, wherein a frequency of at least the first ultrasonic wave is at least 10 MHZ.

31. The method according to claim 24, wherein the portion of the first ultrasonic wave and the portion of the second ultrasonic wave are reflected off substantially a same location on the boundary.

32. A method for measuring the thickness of a medium having a first acoustic velocity and interposing between a first location and a surface boundary with a second material having a second acoustic velocity, the method comprising:
  transmitting a first ultrasonic wave from the first location through the interposing medium to the boundary, wherein the interposing medium comprises a biological tissue;
  measuring a first travel time of a portion of the first ultrasonic wave, the portion of the first ultrasonic wave being reflected off the surface boundary to a second location;
  transmitting a second ultrasonic wave from a third location through the interposing medium to the boundary;
  measuring a second travel time of a portion of the second ultrasonic wave, the portion of the second ultrasonic wave being reflected off the surface boundary to the third location;
  determining the thickness of the interposing medium utilizing a distance between the first and the second locations and the measured first and second travel times for the first and second ultrasonic waves.

33. A method of determining the acoustic velocity of a first soft tissue embedded in a second soft tissue, comprising:
  (a) determining a location of the first soft tissue in the second soft tissue;
  (b) determining an acoustic velocity of the second soft tissue along a first path not passing through the first soft tissue;
  (c) determining a further acoustic velocity of the second soft tissue along a second path passing through the first soft tissue wherein at least one of said paths includes a reflection from an acoustic boundary other than of the first soft tissue; and
  (d) determining the acoustic velocity of the first tissue utilizing the difference between the acoustic velocity and the further acoustic velocity.

34. The method according to claim 33, wherein the first path substantially overlaps a portion of the second path.

35. A method of determining, through an interposing medium, a thickness of a solid, the method comprising:
  transmitting a broadband ultrasonic wave along a path from a first location, through the interposing medium and along a surface of the solid, wherein the interposing medium comprises a biological tissue;
  receiving the ultrasonic wave at a second location;
  analyzing the received ultrasonic wave to determine a difference between a first travel time of high frequency components of the received ultrasonic wave and a second travel time of low frequency components of the received ultrasonic wave; and
  determining said thickness from said difference in travel times.

36. A method for determining, through an interposing medium having a first acoustic velocity, mechanical properties of a solid, underlying the interposing medium, having a surface and having a second acoustic velocity, the method comprising:
  measuring the first acoustic velocity, wherein the interposing medium is a biological tissue;
  measuring an average acoustic velocity of the interposing medium and the solid;
  determining the second acoustic velocity utilizing the first acoustic velocity and determining the mechanical properties from the second acoustic velocity.

37. The method according to claim 36, wherein the measuring comprises:
  transmitting a first ultrasonic wave from a first location through the interposing medium to the surface;
  measuring a first travel time of a portion of the first ultrasonic wave, the portion of the first ultrasonic wave being reflected off the surface to a second location;
  transmitting a second ultrasonic wave from a third location through the interposing medium to the surface;
  measuring a second travel time of a portion of the second ultrasonic wave, the portion of the second ultrasonic wave being reflected off the surface to the third location; and
  determining the first acoustic velocity utilizing the distance between the first and the second locations and the measured first and second travel times for the first and the second ultrasonic waves.

38. A method for determining, through an interposing medium having a first acoustic velocity, mechanical properties of a solid having a surface and having a second acoustic velocity, the method comprising:
  transmitting a first ultrasonic wave along a transmission path from a first location through the interposing medium, along only a short segment of the surface and from the surface through the interposing medium to a second location, wherein the interposing medium comprises a biological tissue;
  measuring a travel time of the first ultrasonic wave; and
  calculating the acoustic velocity in the solid utilizing the measured travel time;
  wherein the length of the short segment is shorter than 1 centimeter.

39. The method according to claim 38, wherein the short segment is shorter than 0.5 centimeters.

40. The method according to claim 39, wherein the short segment is shorter than 0.3 centimeters.

41. The method according to claim 39, wherein the short segment is shorter than 0.15 centimeters.

42. An apparatus for determining an acoustic velocity of a solid having a surface through an interposing medium, comprising:
  an ultrasonic transmitter which generates first waves and second waves into the interposing medium towards the surface, wherein the interposing medium comprises a biological tissue;
  an ultrasonic transmitter/receiver which receives the first waves after the first waves reflect from the surface, which generates third waves into the interposing medium towards the surface, and which receives the third waves after the third waves reflect from the surface;
  an ultrasonic receiver which receives the second waves, the second waves having traveled through the interposing medium, to the surface, along the surface and from the surface to the interposing medium to the ultrasonic receiver; and
  a control unit which controls the ultrasonic transmitter and the transmitter/receiver to generate the first, second and third waves, which receives signals responsive to ultrasonic waves received by the transmitter/receiver and by the receiver, and which determines the shortest travel times of each of the first, second and third waves.

43. An apparatus according to claim 42,
  wherein said ultrasonic receiver is fixedly mounted in a permanent positional relationship relative to said transmitter;
  wherein a portion of the apparatus contacts the living tissue, and wherein the portion extends at a length shorter than or equal to 100 millimeters.

44. The apparatus according to claim 43, wherein the length is shorter than or equal to 50 millimeters.

45. The apparatus according to claim 44, wherein the length is shorter than or equal to 3 millimeters.

46. An apparatus for determining an acoustic velocity of a solid having a surface, comprising:
  an ultrasonic transmitter which generates a first wave into an interposing medium to the surface, wherein the interposing medium comprises a biological tissue;
  an ultrasonic receiver which receives the first wave, the first wave having traveled through the interposing medium to the surface, along the surface and from the surface to the interposing medium to the ultrasonic receiver;
  an ultrasonic unit which generates second waves and receives the second waves reflected from the surface; and
  a control unit which controls the ultrasonic transmitter to generate the first wave the ultrasonic unit to generates the second waves, the control unit receiving signals responsive to the first and second waves received by the receiver and by the ultrasonic unit, and determining a shortest travel times of each of the first and second waves.

47. The apparatus according to claim 46, wherein the ultrasonic unit comprises at least one ultrasonic transmitter/receiver.

48. The apparatus according to claim 47, wherein the at least one transmitter/receiver comprises a transmitter and a receiver.

49. The apparatus according to claim 46, wherein the ultrasonic unit comprises at least two ultrasonic transmitters/receivers.

50. The apparatus according to claim 46, wherein the ultrasonic unit comprises at least three ultrasonic transmitters/receivers.

51. The apparatus according to claim 46, wherein the ultrasonic unit comprises at least four ultrasonic transmitters/receivers.

52. The apparatus according to claim 46, wherein the ultrasonic unit is situated between the ultrasonic receiver and the ultrasonic transmitter.

53. The apparatus according to claim 52, wherein the ultrasonic unit is situated approximately midway between the ultrasonic receiver and the ultrasonic transmitter.

54. The apparatus according to claim 46, wherein the ultrasonic unit is situated substantially closer to one of the ultrasonic receiver and ultrasonic transmitter than to another one of the ultrasonic receiver and ultrasonic transmitter.

55. The apparatus according to claim 46, wherein the control unit calculates the acoustic velocity of the solid.

56. The apparatus according to claim 46, wherein the control unit calculates the acoustic velocity of the interposing medium.

57. The apparatus according to claim 46, wherein the ultrasonic receiver, the ultrasonic transmitter and the ultrasonic unit are not collinear.

58. The apparatus according to claim 46, wherein the ultrasonic receiver, the ultrasonic transmitter and the ultrasonic unit are substantially collinear.

59. The apparatus according to claim 46, wherein at least one of the ultrasonic receiver, the ultrasonic transmitter and the ultrasonic unit is oriented toward the surface at an angle.

60. An apparatus according to claim 46,
wherein at least one ultrasonic transmitter, the ultrasonic receiver and the ultrasonic unit includes a grid of piezoelectric cells which generates and receives ultrasonic waves;
wherein said control unit selectively activates at least one and fewer than all of the cells to act as at least one of said ultrasonic transmitter, said ultrasonic receiver and said ultrasonic unit, and
wherein said velocity of said solid is measured through an interposing medium comprising a biological tissue.

61. The apparatus according to claim 60, wherein at least one of the ultrasonic waves travels along the surface, and wherein the control unit calculates the acoustic velocity of the solid.

62. The apparatus according to claim 60, wherein the control unit calculates the acoustic velocity of the interposing medium.

63. The apparatus according to claim 60, wherein a portion of the apparatus substantially contacts the interposing medium and extends at a length shorter than or equal to 100 millimeters.

64. The apparatus according to claim 63 wherein the length is shorter than or equal to 50 millimeters.

65. The apparatus according to claim 65, wherein the length is shorter than or equal to 3 millimeters.

66. An apparatus for determining an acoustic velocity of a medium interposed between a first location and a solid having a surface, comprising:
an ultrasonic transmitter which generates first waves into the interposing medium towards the surface, wherein the interposing medium comprises a biological tissue;
an ultrasonic transmitter/receiver which receives the first waves after the first waves reflect from the surface and which generates second waves into the interposing medium towards the surface, and which receives the second waves after the second waves reflect from the surface; and
a control unit which controls the ultrasonic transmitter and the transmitter/receiver to generate the first and second waves, the control unit receiving signals responsive to the first and second waves received by the transmitter/receiver and determining shortest travel times of each of the first and second waves.

67. The apparatus according to claim 66, wherein the transmitter/receiver comprises a transmitter which transmits the second wave and a receiver which receives the first and second waves.

68. The apparatus according to claim 60, wherein the control unit selectively activates cells of the grid to generate a scanning ultrasound beam.

69. The apparatus according to claim 67, wherein the first and second waves are reflected off substantially a same location on the surface.

70. A method of determining an acoustic velocity of a hard, in vivo, body tissue, comprising:
providing a hard, in vivo, body tissue; and
determining an acoustic velocity in a portion of the body tissue shorter than about 5 millimeters.

71. The method in accordance with claim 70, wherein the portion is shorter than approximately 3 millimeters.

72. The method in accordance with claim 70, wherein the portion is shorter than approximately 1.5 millimeters.

73. The method in accordance with claim 70, wherein the acoustic velocity is determined in a presence of an intervening softer tissue.

74. The method in accordance with claim 70, wherein the body tissue is a tooth.

75. The method in accordance with claim 70, wherein the body tissue is a curved bone.

76. The method in accordance with claim 70, wherein the body tissue is a vertebra.

77. The method in accordance with claim 70, wherein the body tissue is a portion of a bone situated substantially near a joint.

78. The method in accordance with claim 70, wherein the body tissue is a wrist bone.

79. The method in accordance with claim 70, wherein the body tissue is a bone.

80. The method in accordance with claim 70, further comprising:
after the acoustic velocity is determined, further determining a subsequent acoustic velocity in the portion; and
comparing the first velocity to the subsequent acoustic velocity to determine changes in a structure of the body tissue.

81. The method in accordance with claim 70, wherein the determining step is performed at a predetermined direction on the body tissue, and further comprising:
further determining a perpendicular acoustic velocity in the portion at a second direction, the perpendicular acoustic velocity being substantially perpendicular to the predetermined direction.

82. The method in accordance with claim 70, wherein the portion consists essentially of a surface structure thereof.

83. The method in accordance with claim 70, wherein the body tissue is a femur.

84. A method for determining, through an interposing medium having a first acoustic velocity, mechanical properties of a solid having a surface and having a second acoustic velocity, the method comprising:
transmitting a first ultrasonic wave along a first transmission path from a first location through the interposing medium, along the surface and from the surface to a second location;

measuring a first travel time of the first wave along the first transmission path; and calculating the second acoustic velocity based on the first measured time;

wherein the first and second locations extend along a line which is not parallel to a portion of the first transmission path extending along the surface; and wherein the interposing medium comprises a biological tissue.

85. A method for determining, through an interposing medium having a first acoustic velocity, mechanical properties of a solid having a surface and having a second acoustic velocity, the method comprising:

transmitting at least three ultrasonic waves from at least one of a plurality of ultrasonic transducers towards the surface and back from the surface to at least a second one of the plurality of transducers, wherein at least one of the waves travels along the surface, wherein each one of the ultrasonic waves travels along a different path and wherein the transducers and the solid maintain a single spatial configuration between transmitting of individual ones of the ultrasonic waves;

measuring travel times for the ultrasonic waves; and calculating the second acoustic velocity based on the measured times, wherein the interposing medium comprises a biological tissue.

86. The method according to claim 85, wherein the calculating step comprises plugging the measured times into equations and solving the equations.

87. The method according to claim 86, wherein the equations comprise a set of simultaneous equations.

88. An apparatus for measuring an acoustic velocity of a solid underlying an interposing tissue medium in a living tissue, comprising:

an ultrasonic transmitter;

an ultrasonic receiver; and a control unit which excites the ultrasonic transmitter to transmit an ultrasonic wave through said living tissue to a surface of the solid and back to the ultrasonic receiver, which measures a travel time of the ultrasonic wave and which determines an acoustic velocity of said solid using said measurement, wherein a portion of the apparatus contacts said living tissue, and wherein the portion extends at a length shorter than or equal to 100 millimeters, wherein said ultrasonic transmitter and said ultrasonic receiver are arranged to be on a same side of said living tissue.

89. The apparatus according to claim 88, wherein the length is shorter than or equal to 50 millimeters.

90. The apparatus according to claim 89, wherein the length is shorter than or equal to 3 millimeters.

91. A method of ultrasonic imaging of a body portion having soft tissue overlaying a hard tissue, comprising:

(a) transmitting least one ultrasound beam towards said body portion and receiving an ultrasound beam from said body portion, on a same side of said body portion as said transmitting, thereby ultrasonically scanning a small part of the body portion containing the hard tissue;

(b) determining the acoustic velocity of the contained hard tissue for a determined travel time of said at least one beam; and (c) repeating (a) and (b) on at least a second part of the body portion to determine a map of velocities.

92. A method according to claim 91, wherein said small part is smaller than 10 millimeters.

93. A method according to claim 91, wherein said small part is smaller than 5 millimeters.

94. A method according to claim 91, wherein said small part is smaller than 3 millimeters.

95. A method according to claim 91, wherein said small part is smaller than 1 millimeter.

* * * * *

UNITED STATES PATENT AND TRADEMARK OFFICE
CERTIFICATE OF CORRECTION

PATENT NO.    : 6,221,019 B1
DATED         : April 24, 2001
INVENTOR(S)   : Edward Kantorovich It is certified that error appears in the above-identified patent and that said Letters Patent is hereby corrected as shown below:

Title page,
OTHER PUBLICATIONS, change "Methos" to -- Methods --;

Column 5,
Line 11, change "velocity" to -- velocities --;

Column 6,
Line 31, change "filly" to -- fully --;

Column 8,
Line 48, change "titter" to -- transmitter --;

Column 10,
Line 29, change "knitter" to -- transmitter --;
Line 61, change "long The" to -- long. The --;

Column 11,
Line 5, change "depth Thus" to -- depth. Thus --;
Line 18, change "anus" to -- axis --;
Line 27, change "tibia Thus" to -- tibia. Thus --;
Line 37, change "phi" to -- plurality --;

Column 13,
Line 3, change "cm The" to -- cm. The --;

Column 14,
Line 41, change "descried" to -- described --;

Column 15,
Line 29, change "ample" to -- example --;
Line 50, change "transmitter 90 tissue" to -- transmitter 90 --;
Line 60, change "tissue 22 tissue" to -- tissue 22 --;
Line 61, change "96; tissue and" to -- 96; and --;

Column 16,
Line 24, change "FIG. 7A" to -- FIG. 7A. --;

UNITED STATES PATENT AND TRADEMARK OFFICE
CERTIFICATE OF CORRECTION

PATENT NO.    : 6,221,019 B1
DATED         : April 24, 2001
INVENTOR(S)   : Edward Kantorovich It is certified that error appears in the above-identified patent and that said Letters Patent is hereby corrected as shown below:

Column 17,
Line 28, change "160; tissue and" to -- 160; and --;
Line 37, change "trains" to -- strains --;

Column 18,
Line 24, delete "it"; and

Column 20,
Line 57, change "as" to -- are --.

Signed and Sealed this

Fourth Day of June, 2002

Attest:

JAMES E. ROGAN
Attesting Officer     Director of the United States Patent and Trademark Office